US012116622B2

(12) United States Patent
Perlee et al.

(10) Patent No.: US 12,116,622 B2
(45) Date of Patent: *Oct. 15, 2024

(54) METHODS OF ASSOCIATING GENETIC VARIANTS WITH A CLINICAL OUTCOME IN PATIENTS SUFFERING FROM AGE-RELATED MACULAR DEGENERATION TREATED WITH ANTI-VEGF

(71) Applicant: Regeneron Pharmaceuticals, Inc., Tarrytown, NY (US)

(72) Inventors: Lorah Perlee, Tarrytown, NY (US); Sara Hamon, Tarrytown, NY (US); Charles Paulding, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 406 days.

This patent is subject to a terminal disclaimer.

(21) Appl. No.: 17/325,498

(22) Filed: May 20, 2021

(65) Prior Publication Data

US 2021/0340605 A1  Nov. 4, 2021

Related U.S. Application Data

(63) Continuation of application No. 15/989,371, filed on May 25, 2018, now Pat. No. 11,519,020.

(51) Int. Cl.
*C12Q 1/6827* (2018.01)
*A61K 39/00* (2006.01)
*A61P 27/00* (2006.01)
*C07K 16/28* (2006.01)
*C12Q 1/6809* (2018.01)
*G16B 30/00* (2019.01)
*G16H 50/20* (2018.01)

(52) U.S. Cl.
CPC .... *C12Q 1/6827* (2013.01); *A61K 39/001135* (2018.08); *A61P 27/00* (2018.01); *C07K 16/28* (2013.01); *C12Q 1/6809* (2013.01); *G16B 30/00* (2019.02); *G16H 50/20* (2018.01)

(58) Field of Classification Search
None
See application file for complete search history.

(56) References Cited

U.S. PATENT DOCUMENTS

| | | |
|---|---|---|
| 6,171,586 B1 | 1/2001 | Lam et al. |
| 6,280,593 B1 | 8/2001 | Wiese et al. |
| 6,284,116 B1 | 9/2001 | Wiese et al. |
| 6,303,535 B1 | 10/2001 | Scholz et al. |
| 6,340,778 B1 | 1/2002 | Bueschken et al. |
| 6,436,897 B2 | 8/2002 | Danko et al. |
| 6,455,743 B1 | 9/2002 | Ueda et al. |
| 6,482,972 B1 | 11/2002 | Bahrmann et al. |
| 6,511,583 B1 | 1/2003 | Mueller et al. |
| 6,676,941 B2 | 1/2004 | Thorpe et al. |
| 6,777,429 B1 | 8/2004 | Adam et al. |
| 6,884,879 B1 | 4/2005 | Baca et al. |
| 7,033,604 B2 | 4/2006 | Ueno |
| 7,060,269 B1 | 6/2006 | Baca et al. |
| 7,070,959 B1 | 7/2006 | Papadopoulos et al. |
| 7,303,746 B2 | 12/2007 | Wiegand et al. |
| 7,303,747 B2 | 12/2007 | Wiegand et al. |
| 7,303,748 B2 | 12/2007 | Wiegand et al. |
| 7,306,799 B2 | 12/2007 | Wiegand et al. |
| 7,374,757 B2 | 5/2008 | Papadopoulos et al. |
| 7,374,758 B2 | 5/2008 | Papadopoulos et al. |
| 7,378,095 B2 | 5/2008 | Cao et al. |
| 7,396,664 B2 | 7/2008 | Daly et al. |
| 7,404,278 B2 | 7/2008 | Wittland et al. |
| 7,521,049 B2 | 4/2009 | Wiegand et al. |
| 7,531,173 B2 | 5/2009 | Wiegand et al. |
| 8,092,803 B2 | 1/2012 | Furfine et al. |
| 8,110,546 B2 | 2/2012 | Dix et al. |
| 8,455,701 B2 | 6/2013 | Kaizik et al. |
| 8,563,782 B2 | 10/2013 | Kaizik et al. |
| 8,581,008 B2 | 11/2013 | Kaizik et al. |
| 8,871,985 B2 | 10/2014 | Vilet et al. |
| 9,220,631 B2 | 12/2015 | Sigg et al. |
| 9,254,338 B2 | 2/2016 | Yancopoulos |
| 9,567,276 B2 | 2/2017 | Klasovsky et al. |
| 9,669,069 B2 | 6/2017 | Yancopoulos |
| 9,676,805 B2 | 6/2017 | Dyballa et al. |
| 9,845,276 B2 | 12/2017 | Franke et al. |
| 9,914,681 B2 | 3/2018 | Geilen et al. |
| 10,000,440 B2 | 6/2018 | Reeker et al. |
| 10,130,681 B2 | 11/2018 | Yancopoulos |
| 10,406,226 B2 | 9/2019 | Dix et al. |

(Continued)

FOREIGN PATENT DOCUMENTS

| | | |
|---|---|---|
| CA | 2241319 | 7/1997 |
| CN | 104894261 | 9/2015 |

(Continued)

OTHER PUBLICATIONS

Abedi et al., "Variants in the VEGFA Gene and Treatment Outcome after Anti-VEGF Treatment for Neovascular Age-related Macular Degeneration", Ophthalmology, 2013, 120(1), pp. 115-121.

Agosta et al., "Pharmacogenetics of antiangiogenic and antineovascular therapies of age-related macular degeneration", Pharmacogenomics, 2012, 13(9), pp. 1037-1053.

Francis, "The influence of genetics of response to treatment with ranibizumab (Lucentis) for age-related macular degeneration: the Lucentis Genotype Study (an American Ophthalmological Society thesis)", Transactions of the American Ophthalmological Society Annual Meeting, 2011, 109, pp. 115-156.

Gorin, "Genetic insights into age-related macular degeneration: Controversies addressing risk, causality, and therapeutics", Molecular Aspects of Medicine, 2012, 33(4), pp. 467-486.

(Continued)

*Primary Examiner* — Katherine D Salmon
(74) *Attorney, Agent, or Firm* — Armstrong Teasdale LLP

(57) ABSTRACT

Disclosed herein are methods and compositions for associating a genetic variant with intraretinal fluid. Also disclosed herein are methods and compositions for associating a genetic variant with visual acuity, anatomic outcomes or treatment frequency.

28 Claims, 8 Drawing Sheets

(56) References Cited

U.S. PATENT DOCUMENTS

| | | |
|---|---|---|
| 10,464,992 B2 | 11/2019 | Furfine et al. |
| 10,828,345 B2 | 11/2020 | Yancopoulos |
| 2002/0133047 A1 | 9/2002 | Bahrmann et al. |
| 2003/0003014 A1 | 1/2003 | Metzner et al. |
| 2003/0113316 A1 | 6/2003 | Kaisheva et al. |
| 2003/0138417 A1 | 7/2003 | Kaisheva et al. |
| 2003/0171320 A1 | 9/2003 | Guyer |
| 2004/0197324 A1 | 10/2004 | Liu et al. |
| 2004/0265309 A1 | 12/2004 | Kandel et al. |
| 2005/0043236 A1 | 2/2005 | Daly et al. |
| 2005/0112061 A1 | 5/2005 | Holash et al. |
| 2005/0163798 A1 | 7/2005 | Papadopoulos et al. |
| 2005/0182370 A1 | 8/2005 | Hato |
| 2005/0260203 A1 | 11/2005 | Wiegand et al. |
| 2006/0058234 A1 | 3/2006 | Daly et al. |
| 2006/0172944 A1 | 8/2006 | Wiegand et al. |
| 2006/0217311 A1 | 9/2006 | Dix et al. |
| 2007/0190058 A1 | 8/2007 | Shams |
| 2008/0220004 A1 | 9/2008 | Wiegand et al. |
| 2009/0017029 A1 | 1/2009 | Hoh et al. |
| 2010/0048959 A1 | 2/2010 | Sigl et al. |
| 2011/0159608 A1 | 6/2011 | Graham |
| 2011/0237650 A1 | 9/2011 | Collard et al. |
| 2011/0276005 A1 | 11/2011 | Hioki et al. |
| 2012/0004473 A1 | 1/2012 | Lee et al. |
| 2012/0091026 A1 | 4/2012 | Chacomac et al. |
| 2012/0123169 A1 | 5/2012 | Kaizik et al. |
| 2012/0253083 A1 | 10/2012 | Kaizik et al. |
| 2014/0012227 A1 | 1/2014 | Sigg et al. |
| 2014/0350307 A1 | 11/2014 | Eom et al. |
| 2016/0075621 A1 | 3/2016 | Azhar et al. |
| 2016/0193217 A1 | 7/2016 | Higashi |
| 2016/0236150 A1 | 8/2016 | Geilen et al. |
| 2016/0257634 A1 | 9/2016 | Dyballa et al. |
| 2017/0129838 A1 | 5/2017 | Dyballa et al. |
| 2018/0126361 A1 | 5/2018 | Klasovsky et al. |
| 2018/0208541 A1 | 7/2018 | Boeck et al. |
| 2018/0319727 A1 | 11/2018 | Dyballa et al. |
| 2019/0290725 A1 | 9/2019 | Vitti et al. |
| 2019/0388539 A1 | 12/2019 | Dix et al. |
| 2020/0017572 A1 | 1/2020 | Furfine et al. |

FOREIGN PATENT DOCUMENTS

| | | |
|---|---|---|
| JP | 2010509369 | 3/2010 |
| JP | 2012-080900 | 4/2012 |
| JP | 2013-126422 | 6/2013 |
| JP | 2014-510526 | 1/2014 |
| WO | 1989011298 | 11/1989 |
| WO | 1997004801 | 2/1997 |
| WO | 1997044068 | 11/1997 |
| WO | 1998045331 | 10/1998 |
| WO | 2000058255 | 10/2000 |
| WO | 2000075319 | 12/2000 |
| WO | 2004091658 | 10/2004 |
| WO | 2004106378 | 12/2004 |
| WO | 2005000895 | 1/2005 |
| WO | 2006047325 | 5/2006 |
| WO | 2007022101 | 2/2007 |
| WO | 2007035621 | 3/2007 |
| WO | 2007084765 | 7/2007 |
| WO | 2007149334 | 12/2007 |
| WO | 2008063932 | 5/2008 |
| WO | 2008077155 | 6/2008 |
| WO | 2008154423 | 12/2008 |
| WO | 2009030976 | 3/2009 |
| WO | 2011006877 | 1/2011 |
| WO | 2012097019 | 7/2012 |
| WO | 2012125869 | 9/2012 |
| WO | 2013106765 | 7/2013 |
| WO | 2015006734 | 1/2015 |
| WO | 2017080690 | 5/2017 |

OTHER PUBLICATIONS

Heier et al., "Intravitreal Aflibercept (VEGF Trap-Eye) in Wet Age-related Macular Degeneration", Am Acad Ophthalmology, 2012, 119 (12), pp. 2537-2548.

Kawashima et al., "Effects of aflibercept for ranibizumab-resistant neovascular age-related macular degeneration and polypoidal choroidal vasculopathy", Graefe's Archive for Clinical and Experimental Ophthalmology, 2014, 253(9), pp 1471-1477.

Myers et al., "Optimal Alignments in Linear Space", CABIOS, 1988, 4(1), pp. 11-17.

Needleman et al., "A General Method Applicable to the Search for Similarities in the Amino Acid Sequence of Two Proteins", J Mol Biol, 1970, 48, pp. 443-453.

Wang et al., "Suggestive association between PLA2G12A single nucleotide polymorphism re2285714 and response to anti-vascular endothelial growth factor therapy in patients with exudative age-related macular degeneration" Molecular Vision, 2012, 18, pp. 2578-2585.

International Search Report and Written Opinion for PCT/2016/064403 (WO 17/96031).

McKibbin et al., "Aflibercept in wet AMD beyond the first year of treatment: recommendations by an expert roundtable panel", Eye (Lond), 2015, 29(suppl 1), pp. S1-S11.

Heier et al, "The 1-year Results of CLEAR-IT 2, a Phase 2 Study of Vascular Endothelial Growth Factor Trap-Eye Dosed As-needed After 12-week Fixed Dosing", Ophthalmology, 2011, 118(6), pp. 1098-1106.

Klettner et al., "Comparison of Bevacizumab, Ranibizumab, and Pegaptanib In Vitro: Efficiency and Possible Additional Pathways", Investigative Ophthalmology and Visual Science, 2008, 49(10), pp. 4523-4527.

Semeraro et al., "Pharmacokinetic and Pharmacodynamic Properties of Anti-VEGF Drugs After Intravitreal Injection", Current Drug Metabolism, 2015, 16(7), pp. 572-584.

Malik et al., "Safety profiles of anti-VEGF drugs: bevacizumab, ranibizumab, aflibercept and ziv-aflibercept on human retinal pigment epithelium cells in culture", Br J Ophthalmol, 2014, 98, pp i11-i16.

Zehetner et al., "Systemic Counterregulatory Response of Placental Growth Factor Levels to Intravitreal Aflibercept Therapy", IVOS, 2015, 56(5), pp. 3279-3286.

Ashraf et al., "Aflibercept in age-related macular degeneration: evaluating its role as a primary therapeutic option", Eye, 2017, pp. 1-14.

Stewart et al., "Pharmacokinetic rationale for dosing every 2 weeks versus 4 weeks with intravitreal ranibizumab, bevacizumab, aflibercept (vascular endothelial growth factor trap-eye)", Retina, 2012, 32(3), pp. 434-457.

Cho et al., "Aflibercept for exudative AMD with persistent fluid on ranibizumab and/or bevacizumab", Br J Ophthalmol, 2013, 97, pp. 1032-1035.

Perlee et al., "Identification of Genetic Variants Associated with Anti-VEGF Drug Response in Neovascular AMD Patients in the VIEW Trail", 2016, ARVO Annual Meeting Abstract.

Arakawa et al., "Factors Affecting Short-Term and Long-TermStabilities of Proteins", Advanced Drug Delivery Reviews, 1993, 10, pp. 1-28.

Arakawa et al., "Recombinant Production of Native Proteins from *Escherichia coli*", Rational Design of Stable Protein Formulations Theory and Practice, 2002, Springer Science+Business Media, pp. 27-60.

Brent et al., "Physical Stabilization of Proteins in Aqueous Solution", Raional Design of Stable Protein Formulations Theory and Practice, 2002, Springer Science+Business Media, pp. 61-84.

Meyer et al., "Effects of Conformation on the Chemical Stability of Pharmaceutically Relevant Polypeptides", Rational Design of Stable Protein Formulations Theory and Practice, 2002, Springer Science+Business Media, pp. 85-108.

(56) References Cited

OTHER PUBLICATIONS

Powell et al., "Compendium of Excipients for Parenteral Formulations", PDS J Pharm Sci and Tech, 1998, 52, pp. 238-311.
Bontempo "Preformulation Development of Parenteral Biopharmaceuticals", Development of Biopharmaceutical Parenteral Dosage Forms, 1997, Chapter 4, pp. 91-108.
Defelippis et al., "Peptides and Prote ins as Parenteral Suspensions: an Overview of Design,Development, and Manufacturing Considerations", Pharmaceutical Formulation Development of Peptides and Proteins, 2000, Chapter 7, pp 113-144.
Rowe et al., "Glycerin", Handbook of Pharmaceutical Excipients, 2003 4th Ed, pp. 257-259.
Rowe et al., "Mannitol", Handbook of Pharmaceutical Excipients, 2003, 4th Ed, pp. 373-377.
Rowe et al., "Polyethylene Glycol", Handbook of Pharmaceutical Excipients, 2003, 4th Ed, pp. 454-459.
Rowe et al., "Polyoxyethylene Sorbitan Fatty Acid Esters", Handbook of Pharmaceutical Excipients, 2003, 4th Ed, pp. 479-483.
Rowe et al., "Potassium Chloride", Handbook of Pharmaceutical Excipients, 2003, 4th Ed, pp. 497-499.
Rowe et al., "Propylene Glycol", Handbook of Pharmaceutical Excipients, 2003, 4th Ed, pp. 521-523.
Rowe et al., "Sodium Chloride", Handbook of Pharmaceutical Excipients, 2003, 4th Ed, pp. 556-559.
Rowe et al., "Sodium Phosphate, Dibasic", Handbook of Pharmaceutical Excipients, 2003, 4th Ed, pp. 574-576.
Rowe et al., "Sodium Phosphate, Monobasic", Handbook of Pharmaceutical Excipients, 2003, 4th Ed, pp. 577-578.
Rowe et al., "Sorbitol", Handbook of Pharmaceutical Excipients, 2003, 4th Ed, pp. 596-599.
Rowe et al., "Sucrose", Handbook of Pharmaceutical Excipients, 2003, 4th Ed, pp. 622-625.
Rowe et al., "Trehalose", Handbook of Pharmaceutical Excipients, 2003, 4th Ed, pp. 657-658.
Akers et al., "Peptides and Proteins as ParenteralSolutions", Pharmaceutical Formulation Development of Peptides and Proteins, 1999, Taylor & Francis, Ch 8, pp. 145-177.
Akers et al., "Formulation Development of Protein Dosage Forms", Development and Manufacture of Protein Pharmaceuticals, 2002, Kluwer Academic/Plenum Publishers, Ch 2, pp. 47-127.
Remicade Product Label dated Dec. 1, 2000, pp. 1-18.
Raptiva, Center for Drug Evaluation and Research Approval Package for Application No. STN/BLA 125075/0, Approved Product Label for RAPTIVA Product Label dated 2003, pp. 1-20.
Brange, "Physical Stability of Proteins", Pharmaceutical Formulation Development of Peptides and Proteins, 1999, Taylor & Francis, Ch 6, pp. 89-112.
Pearlman et al., "Pharmaceutics of protein drugs", Journal of Pharmacy and Pharmacology, 1992, 44(Suppl 1), pp. 178-185.
Chang et al., "Surface-Induced Denaturation of Proteins duringFreezing and its Inhibition by Surfactants", J Pharm Sci, 1996, 85, pp. 1325-1330.
Chang et al., "Practical Approaches to Protein Formulation Development", Rational Design of Stable Protein Formulations Theory and Practice, 2002, Springer Science+Business Media, pp. 1-26.
Chirila et al., "The Vitreous Humor", Handbook of Biomaterial Properties, 1998, Chapman & Hall, pp. 125-131.
Garcia-Valldecabres et al., "pH Stability of ophthalmic solutions", Optometry, 2004, 75, pp. 161-168.
Gerber et al., "Complete Inhibition ofRhabdomyosarcoma Xenograft Growth and Neovascularization Requires Blockade of Both Tumor and Host Vascular Endothelial Growth Factor", Cancer Res, 2000, 60, pp. 6253-6258.
Hovgaard et al., "Protein Purifcation", Pharmaceutical Formulation Development of Peptides and Proteins, 1999, Taylor & Francis, Ch 3, pp. 29-40.
Kreilgaard et al., "Effect of Tween 20 on Freeze-Thawing- and Agitation-Inducted Aggregation of Recombinant Human Factor XIIP", J Pharm Sci, 1998, 87, pp. 1597-1603.
Macugen Product Monograph, 2005, pp. 1-34.
Patro et al., "Protein formulation and fill finish operations", Biotechnology Annual Review, 2002, 8, pp. 55-84.
Nayar et al., "High Throughput Formulation: Strategies for Rapid Development of Stable Protein Products" Rational Design of Stable Protein Formulations Theory and Practice, 2002, Springer Science+Business Media, pp. 177-198.
Nema et al., "Excipients and Their Use in Injectable Products", PSD J Pharm Sci and Tech, 1997, 51, pp. 166-171.
Ohba, "Effects of Tonicity on the Pacemaker Activity of Guinea-pig Sino-atrial Node", Japanese Journal of Physiology, 1986, 36, pp. 1027-1038.
European Pharmacopoeia, 4:1.3 "Buffer solutions", 5th Edition, Main vol. 5.0, 2005, pp. 431-434.
Parkins et al., "The formulation of biopharmaceutical products", Pharmaceutical Science & Technology Today, 2000, 3(4), pp. 129-137.
Frampton "Afbercept for Intravitreal injection In Neovascular Age-Related Macular Degeneration", Drugs, 2012, 29, pp 839-846.
Stoll et al., "General Methods for Handling Proteins and Enzymes—Buffers: Principles and Practice", Methods in Enzymology, 1990, 182, pp. 24-38.
Sweetana et al., "Solubility Principles and Practices for Parenteral Drug Dosage Form Development", PDA J Pharm Sci and Tech, 1996, 50, pp. 330-342.
Templeton et al., "New Directions in Liposome Gene Delivery", Molecular Biology, 1999, 11, pp. 175-180.
Wang, "Instability, stabilization, and formulation of liquid protein pharmaceuticals", Int. J Pharm, 1999, 185, pp. 129-188.
Apte et al., "A Review and Classifcation of Emerging Excipients in Parenteral Medications", Pharmaceutical Technology, 2003, pp. 46-60.
Avastin, Center for Drug Evaluation and Research Approval Package for Application No. STN-125085/0, Approved Product Label for AVASTIN, 2004, pp. 1-12.
McGoff et al., "Solution Formulation of Proteins/Peptides", Protein Formulation and Delivery, 1989, pp. 139-158.
Cappola, "Freeze-Drying Concepts: The Basics", Protein Formulation and Delivery, 2000, Chapter 6, pp. 159-199.
Carpenter, "Rational Designof Stable Lyophilized Protein Formulations: Somne Practical Advice", Pharmaceutical Research, 1997, 14(8), pp. 969-975.
Manning et al., "Stability of protein pharmaceuticals", Pharmaceutical Research, 1989, 6(11), pp. 903-918.
Fraser et al., "Single Injections of Vascular Endothelial Growth Factor Trap Block Ovulation in the Macaque and Produce a Prolonged, Dose-Related Suppression of Ovarian Function", The Journal of Clinical Endocrinology & Metabolism, 2005, 90(2), pp. 1114-1122.
Frokjaer et al., "Protein drug stability: a formulation challenge", Nature Reviews Drug Discovery, 2005, 4, pp. 298-306.
Gaudreault et al., "Preclinical Pharmacokinetics of Ranibizumab (rhuFabV2) afer a Single Intravitreal Administration", Investigative Ophthalmology & Visual Science, 2005, 46(2), pp. 726-733.
Lee et al., "Topical Ocular Drug Delivery: Recent Developments and Future Challenges", Journal of Ocular Pharmacology, 1986, 2(1), pp. 67-108.
HERCEPTIN Product Label dated Sep. 1998, pp. 1-2.
Husain et al., "Safety and Effcacy of Intravitreal Injection of Ranibizumab in Conbination With Verteporfin PDT on Experimental Choroidal Neovascularization in the Monkey", Archives of Ophthalmology, 2005, 123(4), pp. 509-516.
Wickremasinghe et al., "Variants in the APOE Gene Are Associated with Improved Outcome after Anti-VEGF Treatment for Neovascular AMD", Investigative Ophthalmology & Visual Science, 2011, 52(7), pp. 4072-4079.
Lin et al., "Vascular Endothelial Growth Factor Gene Polymorphisōms in Age-related Macular Degeneration", American Journal of Ophthalmology, 2008, 145(6), pp. 1045-1051.e.1.
Li et al., "PRKX critically regulates endothelial cell proliferation, migration, and vascular-like structure formation", Developmental Biology, 2011, 356, pp. 475-485.

(56) References Cited

OTHER PUBLICATIONS

Lee et al., "Pharmacogenetics of Complement Factor H (Y402H) and treatment of exudative age-related macular degeneration with ranibizumab", British Journal of Ophthalmology, 2009, 93(5), pp. 610-613.

Kondo et al., "LOC387715/HTRA1 Variants in Polypoidal Choroidal Vasculopathy and Age-related Macular Degeneration in a Japanese Population", American Journal of Ophthalmology, 2007, 144(4), pp. 608-612.

Kloeckener-Gruissem et al., "Genetic Association with Response to Intravitreal Ranibizumab in Patients with Neovascular AMD", Investigative Ophthalmology & Visual Science, 2011, 52(7), pp. 4694-4702.

Klein et al., "Complement Factor H Polymorphism in Age-Related Macular Degeneration", Science, 2005, 308(5720), pp 385-389.

Lotery et al., "Pharmacogenetic Associations with Vascular Endothelial Growth Factor Inhibition in Participants with Neovascular Age-related Macular Degeneration in the IVAN Study", Ophthalmology, 2013, 120(12), pp. 2637-2643.

Imai et al., "CFH, VEGE, and PEDF genotypes and the response to intravitreous injection of bevacizumab for the treatment of age-related macular degeneration", Journal of Ocular Biology, Diseases, and Informatics, 2010, 3, pp. 53-59.

Nakata et al., VEGF gene polymorphism and response to intravitreal bevacizumab and triple therapy in age-related macular degeneration, Japanese Journal of Ophthalmology, 2011, 55, pp. 435-443.

Hermann et al., "Polymorphisms in Vascular Endothelial Growth Factor Receptor 2 Are Associated with Better Response Rates to Ranibizumab Treatmentin Age-related Macular Degeneration", Ophthalmology, 2014, 121(4), pp. 905-910.

Hautamaki et al. "Interleukin 8 promoter polymorphism predicts the initial response to bevacizumab treatment for exudative age-related macular degeneration", Retina, 2013, 33(9), pp. 1815-1827.

Fuse et al., "Polymorphisms in ARMS2 (LOC387715) and LOXLI Genes in the Japanese With Age-Related Macular Degeneration", American Journal of Ophthalmology, 2011, 151(3), pp. 550-556.

Non-Final Office Action dated Apr. 26, 2022 in related U.S. Appl. No. 15/995,518.

Notice of Allowance dated Sep. 7, 2022 in related U.S. Appl. No. 15/995,518.

Notice of Allowance dated Jul. 7, 2022 in related U.S. Appl. No. 15/989,371.

Information from ClinicalTrials.gov archive History of Changes for Study: NCT00509795 "Double-Masked Study of Efficacy and Safety of IVT VEGF Trap-Eye in Subjects With Wet AMO (VIEW 1 )", Latest version submitted Dec. 20, 2012 on ClinicalTrials.gov (NCT00509795_2012).

Information from ClinicalTrials.gov archive History of Changes for Study: NCT00527423 "Randomized, Single-Masked, Long-Term, Safety and Tolerability Study of VEGF Trap-Eye in AMO", Latest version submitted Nov. 1, 2011 on ClinicalTrials.gov (NCT00527423_2007-2011).

Information from ClinicalTrials.gov archive History of Changes for Study: NCT00527423 "Randomized, Single-Masked, Long-Term, Safety and Tolerability Study of VEGF Trap-Eye in AMO", Latest version submitted Jun. 10, 2013 on ClinicalTrials.gov (NCT00527423_2012-2013).

Information from ClinicalTrials.gov archive History of Changes for Study: NCT00637377 "Vascular Endothelial Growth Factor (VEGF) Trap-Eye: Investigation of Efficacy and Safety in Wet Age-Related Macular Degeneration (AMO) (VIEW 2)", Latest version submitted Dec. 16, 2011 on ClinicalTrials.gov (NCT00637377_2008-2011).

Information from ClinicalTrials.gov archive History of Changes for Study: NCT00637377 "Vascular Endothelial Growth Factor (VEGF) Trap-Eye: Investigation of Efficacy and Safety in Wet Age-Related Macular Degeneration (AMO) (VIEW 2)", Latest version submitted Nov. 28, 2014 on ClinicalTrials.gov (NCT00637377_2012-2014).

clinicaltrials.gov/ct2/show/NCT00509795, Dec. 28, 2012, pp. 1-10. The present application discloses results and observations from a genome wide association study (GWAS) analysis of approximately 1 million genetic variants performed on a subset of patients in a clinical trial called VIEW 1 (VEGF Trap-Eye: Investigation of Efficacy and Safety in Wet AMD). This VIEW 1 trial was a randomized, double-masked, Phase III.

clinicaltrials.gov/ct2/show/NCT00637377, Dec. 12, 2014, pp. 1-11. In parallel with the VIEW 1 trial, Bayer HealthCare, a third party collaborator of Regeneron, carried out a second clinical trial, called VIEW 2, on a different patient population in Europe, Asia Pacific, Japan, and Latin America. After the present application was filed, and at Regeneron's request, Bayer HealthCare conducted a GWAS analysis on the.

investor.regeneron.com/news-releases/news-release-details/two-year-results-phase-3-studies-eyleatm-aflibercept-injection, Dec. 5, 2011, pp. 1-4.

Abraham et al., "Randomized, Double-Masked, Sham-Controlled Trial of Ranibizumab for Neovascular Age-Related Macular Degeneration: PIER Study Year 2", Am J Ophthalmol, 2010, 150, pp. 315-324.

Levine et al., "Macular Hemorrhage In Neovascular Age-Related Macular Degeneration After Stabilization With Antiangiogenic Therapy", Retina, 2009, 29(8), pp. 1074-1079.

Barbazetto, et al., "Dosing Regimen And The Frequency Of Macular Hemorrhages In Neovascular Age-Related Macular Degeneration Treated With Ranibizumab" Retina, 2010, 30(9), pp. 1376-1385.

Michels et al., "Systemic Bevacizumab (Avastin) Therapy for Neovascular Age-Related Macular Degeneration", Ophthalmology, 2005, 112, pp. 1035-1047.

Rosenfeld, "Ranibizumab for Neovascular Age-Related Macular Degeneration." N Engl J Med, 2006, 355(14), pp. 1419-1431.

Brown et al., "Ranibizumab versus Verteporfin Photodynamic Therapy for Neovascular Age-Related Macular Degeneration: Two-Year Results of the ANCHOR Study", Ophthalmology, 2009, 116, pp. 57-65.

Prager et al., "Intravitreal bevacizumab (Avastin) for macular oedema secondary to retinal vein occlusion: 12-month results of a prospective clinical trial", Br. J Ophthalmol, 2009, 93, pp. 452-456.

Brown, "Clinical Implications of the BRAVO and CRUISE Trials", Retina Today, 2010, pp. 38-40.

Genentech, "FDA Approves Genentech's Lucentis (Ranibizumab Injection) Prefilled Syringe", Press Release, 2016, pp. 1-4.

Nagpal et al., "A comparative debate on the various anti-vascular endothelial growth factor drugs: Pegaptanib sodium (Macugen), ranibizumab (Lucentis) and bevacizumab (Avastin)", Indian J Ophthalmol, 2007, 55, pp. 437-439.

Shibuya, "Vascular Endothelial Growth Factor (VEGF) and Its Receptor (VEGFR) Signaling in Angiogenesis: A Crucial Target for Anti- and Pro-Angiogenic Therapies", Genes and Cancer, 2011, 2(12), pp. 1097-1105.

Colucciello, "Prefilled Syringe Delivery of Intravitreal Anti-VEGF Medications", Retinal Physician, 2019, pp. 1-6.

Merani et al., "Endophthalmitis following intravitreal anti-vascular endothelial growth factor (VEGF) injection: a comprehensive review", Int J Retin Vitr, 2015, 1(9), pp. 1-19.

Peyman et al., "Intravitreal injection of therapeutic agents", Retina, 2009, 29, pp. 875-912.

FDA, "Highlights of Prescribing Information: TRIVARIS", NDA-22-220, 2008, pp. 1-15.

Kim et al., "A Brief History of Anti-VEGF for the Treatment of Ocular Angiogenesis", ASIP Centennial Commentary, American Journal of Pathology, 2012, 181(2), pp. 376-379.

FDA, "Highlights of Prescribing Information: Eylea", 2011, pp. 1-15.

Dixon et al., "VEGF Trap-Eye for the treatment of neovascular age-related macular degeneration", Exper Opin Investig Drugs, 2009, 18(10), pp. 1573-1580.

Falkner-Radler et al., "Needle Size in Intravitreal Injections-Preliminary Results of a Randomized Clinical Trial", ARVO Annual Meeting Abstract, Investigative Ophthalmology and Visual Science, 2012, 53(884), pp. 1-2.

FDA, "Highlights of Prescribing Information: Lucentis", 2010, pp. 1-7.

(56) References Cited

OTHER PUBLICATIONS

Liu et al., "Silicone Oil Microdroplets and Protein Aggregates in Repackaged Bevacizumab and Ranibizumab: Effects of Long-term Storage and Product Mishandling", IOVS, 2011, 52(2), pp. 1023-1034.
Drugs.com, "Macugen", 2011 http://web.archive.org/web/20110307065238/http://drugs .com:80/pro/macugen.html, pp. 1-11.
Stewart et al., "Aflibercept", Nature Reviews Drug Discovery, 2012, 11, pp. 269-270.
Wang, "Protein aggregation an its inhibition in biopharmaceuticals", International Journal of Pharmaceutics, 2005, 289, pp. 1-30.
Bogard et al., "Practical Considerations in the Production, Purification, and Formulation of Monoclonal Antibodies for Immunoscintigraphy and Immunotherapy", Seminars in Nuclear Medicine, 1989, vol. XIX No. 3, pp. 202-220.
Shukla et al., "Protein aggregation kinetics during Protein A chromatography Case study for an Fc fusion protein", Journal of Chromatography A, 2007, 1171, pp. 22-28.
Hossler et al., "Optimal and consistent protein glycosylation in mammalian cell culture", Glycobiology, 2009, 19(9), pp 936-949.
Jefferis, "Glycosylation of Recombinant Antibody Therapeutics", Biotechnol Prog, 2005, 21, pp. 11-16.
Fast et al., "Physical Instability of a Therapeutic Fc Fusion Protein: Domain Contributions to Conformational and Colloidal Stability", Biochemistry, 2009, 48(49), pp. 11724-11736.
Souillac, "Biophysical Characterization of Insoluble Aggregates of Multi-Domain Protein: An Insight into the Role of the Various Domains", Journal of Pharmaceutical Sciences, 2005, 94(9), pp. 2069-2083.
Moroney et al., "Aflibercept in epithelial ovarian carcinoma", Future Oncol, 2009, 5(5), pp. 591-600.
Chamow et al., "Antibody Fusion Proteins", 1990, pp. 221-309.
Shukla et al., "Chapter 4: Downstream Processing of Fc-Fusion Proteins", Therapeutic Fc-Fusion Proteins, 2014, pp. 97-114.
Wang et al., "Antibody Structure, Instability, and Formulation", Journal of Pharmaceutical Sciences, 2007, 96(1), pp. 1-26.
Winter et al., "Man-made antibodies", Nature, 1991, 349, pp. 293-299.
Andersen et al., "Recombinant protein expression for therapeutic applications", Biochemical Engineering, 2002, 13, pp 117-123.
Genentech, "XOLAIR", 2003, pp. 1-17.
Wulff et al., "Prevention of Thecal Angiogenesis, Antral Follicular Growth, and Ovulation in the Primate by Treatment with Vascular Endothelial Growth Factor Trap R1R2", Endocrinology, 2002, 143(7), pp. 2797-2807.
Rudge et al., "VEGF Trap as a Novel Antiangiogenic Treatment Currently in Clinical Trials for Cancer and Eye Diseases, and VelociGene®-based Discovery of the Next Generation of Angiogenesis Targets", Cold Spring Harbor Symposia on Quantitative Biology, 2005, vol. LXX, pp. 411-418.
FDA, "Highlights of Prescribing Information", Remicade 2013, pp. 1-58.
Randolph et al., "Chapter 7: Surfactant-Protein Interactions", Rational Design of Stable Protein Formulations, 2002, pp 159-175.
FDA "Highlights of Prescribing Information", Lucentis, 2014, pp. 1-14.
Janeway et al., "The structure of a typical antibody", Immunobiology: The immune system in health and disease, 5th edition, 2001, pp. 1-6.
Regenbase, "Controls in SCI experiments", 2016, pp. 1-2.
Fraser et al., "Single Injections of Vascular Endothelial Growth Factor Trap Block Ovulation in the Macaque and Produce a Prolonged, Dose-Related Suppression of Ovarian Function", The Journal of Clinical Endocrinology and Metabolism, 2005, 90(2), pp. 1114-1122.
Genentech, "Herceptin", 1998, pp. 1-2.
Genentech, "Raptiva", 2009, pp. 1-36.
Avastin "Highlights of Prescribing Information", 2017, pp. 1-37.

Chi et al., "Physical Stability of Proteins in Aqueous Solution: Mechanism and Driving Forces in Nonnative Protein Aggregation", Pharmaceutical Research, 2003, 20(9), pp. 1325-1336.
Kocabora et al., "Intravitreal silicone oil droplets following pegaptanib injection", Acta Ophthalmologica, 2010, D22, pp. e44-e45.
Heier, "Intravitreal VEGF Trap for AMD: An Update, The CLEAR-IT 2 Extension Study" Presented at the annual meeting of the Association for Research in Vision and Ophthalmology, Retina Today, 2009, pp. 44-45.
Third Party Submissions dated May 1, 2019 in U.S. Appl. No. 16/055,847.
Third Party Submissions dated May 31, 2019 in U.S. Appl. No. 16/159,282.
Kent, "Anti-VEGF 2019: The State of the Art", Review of Ophthalmology, 2019, pp. 28-35.
Bayer Investor News, "Bayer and Regeneron Start additional Phase 3 Study for VEGF Trap-Eye in Wet Age-related Macular Degeneration.", May 8, 2008, pp. 1-5.
Bayer Investor News, "VEGF Trap-Eye: New Data Confirm Successes in the Treatment of Age-related Macular Degeneration", Sep. 28, 2008, pp. 1-5.
Boyer et al., "A Phase IIIb Study to Evaluate the Safety of Ranibizumab in Subjects with Neovascular Age-related Macular Degeneration", Ophthalmology, 2009, 116(9), pp. 1731-1739.
Brown et al., "Ranibizumab versus Verteporfin for Neovascular Age-Related Macular Degeneration", N Engl J Med, 2006, 355(14), pp. 1432-1444.
Brown et al., "Primary Endpoint Results of a Phase II Study of Vascular Endothelial Growth Factor Trap-Eye in Wet Age-related Macular Degeneration", Ophthalmology, 2011, 118(6), pp. 1089-1097.
Brown et al., "Long-term Outcomes of Ranibizumab Therapy for Diabetic Macular Edema: The 36-Month Results from Two phase III Trials", Ophthalmology, 2013, 120(10), pp. 2013-2022.
Browning et al. "Aflibercept for age-related macular degeneration: a game-changer or quiet addition?", American Journal of Ophthalmology, 2012, 154(2), pp. 222-226.
Campochiaro et al., "Ranibizumab for Macular Edema Due to Retinal Vein Occlusions Implication of VEGF as a Critical Stimulator", Molecular Therapy, 2008, 16(4), pp. 791-799.
Campochiaro et al., "Ranibizumab for Macular Edema following Branch Retinal Vein Occlusion: six-month primary end point results of a phase III study" Ophthalmology, 2010, 117(6), pp. 1102-1112.
Campochiaro et al., "Sustained Benefits from Ranibizumab for Macular Edema following Central Retinal Vein Occlusion: Twelve-Month Outcomes of a phase III Study", Ophthalmology, 2011, 188(10), pp. 2041-2049.
Cao et al., "A Subretinal Matrigel Rat Choroidal Neovascularization (CNV) Model and Inhibition of CNV and Associated Inflammation and Fibrosis by VEGF Trap" Investigative Ophthalmology & Visual Science, 2010, 51(11), pp. 6009-6017.
Center for Drug Evaluation and Research Application No. 21-756 Medical Review(s), Dec. 17, 2004, URL:https://www.accessdata.fda.gov/drugsatfda_docs/nda/2004/21-756 Macugen medr.pdf.
Center for Drug Evaluation and Research BLA Application No. 125156 Medical Review, Jun. 2006, URL:https://www.accessdata.fda.gov/drugsatfda_docs/nda/2006/125156s000_Lucentis_ MedR.pdf.
Charles, Steve (Guest Lecturer), "VEGF Trap Has Positive DME Data" Tenth Annual Retina Fellows Forum Jan. 29 and 30, Chicago, Article Date Mar. 1, 2010, pp. 1-6.
Chatziralli et al., "Intravitreal aflibercept for neovascular age-related macular degeneration in patients aged 90 years or older: 2-year visual acuity outcomes", Eye, 2018, 32, pp. 1523-1529.
Chung et al., "Ziv-aflibercept: A novel angiogenesis inhibitor for the treatment of metastatic colorectal cancer", Am J Heath-Syst Pharm, 2013, 70, pp. 1887-1896.
Cooper et al., "Increased Renal Expression of Vascular Endothelial Growth Factor (VEGF) and Its Receptor VEGFR-2 in Experimental Diabetes", Diabetes, 1999, 48, pp. 2229-2239.
Croll et al., "VEGF-mediated inflammation precedes angiogenesis in adult brain", Experimental Neurology, 2004, 187, pp. 388-402.

(56) References Cited

OTHER PUBLICATIONS

DeVriese et al., "Antibodies against Vascular Endothelial Growth Factor Improve Early Renal Dysfunction in Experimental Diabetes", J Am Soc Nephrol, 2001, 12, pp. 993-1000.

Dixon et al., "VEGF Trap-Eye for the treatment of neovascular age-related macular degeneration", Expert Opin Investig Drugs, 2009, 18(10), pp. 1573-1580.

Do et al., "Results of a Phase 1 Study of Intravitreal VEGF Trap in Subjects with Diabetic Macular Edema: The CLEAR-IT DME Study", ARVO Annual Meeting Abstract, May 2007, pp. 1-2.

Eichten et al., "Rapid decrease in tumor perfusion following VEGF blockade predicts long-term tumor growth Inhibition in preclinical tumor models", Angiogenesis, 2013, 16, pp. 429-441.

Engelbert, "The Treat and Extend' Dosing Regimen of Intravitreal Anti-Vascular Endothelial Growth Factor Therapy for Neovascular Age-Related Macular Degeneration." Ophthalmology Management, Issue 42, Jun. 2010, available at http://www.visioncareprofessional.com/emails/amdupdate/index.asp?issue=42.

Eremina et al., "Glomerular-specific alterations of VEGF—A expression lead to distinct congenital and acquired renal diseases", Journal of Clinical Investigation, 2003, 111(5), pp. 707-716.

Flyvbjerg et al., "Amelioration of Long-Term Renal Changes in Obese Type 2 Diabetic Mice by a Neutralizing Vascular Endothelial Growth Factor Antibody", Diabetes, 2002, 51, pp. 3090-3094.

Garcia-Quintanilla et al., "Pharmacokinetics of Intravitreal Anti-VEGF Drugs in Age-Related Macular Degeneration", Pharmaceutics, 2019, 11(365), pp. 1-22.

Gomez-Manzano et al., "VEGF Trap induces antiglioma effect at different stages of disease", Neuro-Oncology, 2008, 10, pp. 940-945.

Gragoudas et al., "Pegaptanib for Neovascular Age-Related Macular Degeneration." N Engl J Med, 2004, 351(27), pp. 2805-2816.

Gutierrez et al., "Intravitreal bevacizumab (Avastin) in the treatment of macular edema secondary to retinal vein occlusion", Clin Ophthalmol, 2008, 2(4), pp. 787-791.

Heier et al., "CLEAR-IT 2: Phase 2, Randomized Controlled Dose and Interval-Ranging Study of Intravitreal VEFG Trap Eye in Patients with Neovascular Age-Related Macular Degeneration: Predictive Factors for Visual Acuity", ARVO Annual Meeting Abstract, Apr. 2009, pp. 1-2.

Heier et al., "RhuFab V2 in Wet AMO—6 Month Continued Improvement Following Multiple Intravitreal Injections", Invest Ophthalmol Vis Sci, 2003, 44(E-Abstract), pp. 1-2.

Heier et al., "Intravitreal Aflibercept (VEGF Trap-Eye) in Wet Age-related macular Degeneration", Ophthalmology, 2012, 119, pp. 2537-2548.

Heier et al., "The 1-year Results of CLEAR-IT 2, a Phase 2 Study of Vascular Endothelial Growth Factor Trap-Eye Dosed As-needed After 12-week Fixed Dosing", Ophthalmology, 2011, 118, pp. 1098-1106.

Heier et al., "The 1-year Results of CLEAR-IT 2, a Phase 2 Study of Vascular Endothelial Growth Factor Trap-Eye Dosed As-needed After 12-week Fixed Dosing: Erratum", Ophthalmology, 2011, 118, pp. 1700.

Holash et al., "VEGF-Trap: A VEGF blocker with potent antitumor effects", PNAS, 2002, 99(17), pp. 11393-11398.

Anonymous "Lucentis (rangibizymab injection) Intravitreal Injection" pp. 103 (Jun. 2006).

Do et al., "An exploratory study of the safety, tolerability and bioactivity of a single intravitreal injection of vascular endothelial growth factor Trap-Eye in patients with diabetic macular oedema", Br J Ophthalmol, 2009, 93(2), pp. 144-149.

Do et al., "The Da Vinci Study: phase 2 primary results of VEGF Trap-Eye in patients with diabetic macular edema", Ophthalmology, 2011, 118(9), pp. 1819-1826.

Do et al., "One-Year Outcomes of the Da Vinci Study of VEGF Trap-Eye in Eyes with Diabetic Macular Edema", Ophthalmology, 2012, 119(8), pp. 1658-1665.

Do et al., "VEGF Trap-Eye Vision-specific Quality of Life through 52 Weeks in Patients with Neovascular AMO in CLEAR-IT 2: A Phase 2 Clinical Trial", ARVO Annual Meeting Abstract, Apr. 2009, pp. 1-2.

Eriksson et al., "Structure, Expression and Receptor-Binding Properties of Novel Vascular Endothelial Growth Factors", Vascular Growth Factors and Angiogenesis, Springer, 1999, pp. 41-57.

The Eyetech Study Group, "Anti-Vascular Endothelial Growth Factor Therapy for Subfoveal Choroidal Neovascularization Secondary to Age-related Macular Degeneration", American Academy of Ophthalmology, 2003, 110(5). pp 979-986.

Ferrara, "Vascular Endothelial Growth Factor: Molecular and Biological Aspects", Advances in Organ Biology, 1999, pp. 1-30.

Gale et al., "Complementary and Coordinated Roles of the VEGFs and Angiopoietins during Normal and Pathologic Vascular Formation" Cold Spring Harbor Symposia on Quantitative Biology, 2002, vol. LXVIL, DD, pp. 267-273.

Haller et al., "VEGF Trap-Eye In CRVO: Primary Endpoint Results of the Phase 3 Copernicus Study", ARVO Annual Meeting Abstract, Apr. 2011, pp. 1-2.

Heier et al., "rhuFab V2 (an anti-VEGF Antibody Fragment) in Neovascular AMD: Safety and Tolerability of Multiple Intravitreal Injections" ARVO Annual Meeting, Dec. 2002, pp. 1-2.

Heier et al., "Intravitreal Aflibercept for Diabetic Macular Edema: 148-Week Results from the VISTA and VIVID Studies", Ophthalmology, 2016, 123(11), pp. 2376-2385.

Holash et al., "Vessel Cooption, Regression, and Growth in Tumors Mediated by Angiopoietins and VEGF", Science, 1999, 284(5422), pp. 1994-1998.

Holash et al., "Inhibitors of growth factor receptors, signaling pathways and angiogenesis as therapeutic molecular agents", Cancer Metastasis, 2006, 25, pp. 243-252.

Kaiser, "Vascular endothelial growth factor Trap-Eye for diabetic macular oedema" Br J Ophthalmol, 2009, 93(2), pp. 135-136.

Krzystolik et al., "Prevention of Experimental Choroidal Neovascularization With Intravitreal Anti-Vascular Endothelial Growth Factor Antibody Fragment", Arch Ophthalmol, 2002, 120, pp. 338-346.

Lawani et al., "A Variable-dosing Regimen with Intravitreal Ranibizumab for Neovascular Age-related Macular Degeneration: Year 2 of the PrONTO Study", Am J Ophthalmology, 2009, 148(1), pp. 43-58.

Mitchell, "Targeted Therapy for Metastatic Colorectal Cancer: Role of Aflibercept", Clinical Colorectal Cancer, 2013, 12(2), pp. 73-85.

Mitra et al., "Review of anti-vascular endothelial growth factor therapy in macular edema secondary to central retinal vein occlusions", Expert Review in Ophthalmol, Taylor & Francis, GB, 2011, 6(6), pp. 623-629.

Mousa et al., "Current Status of Vascular Endothelial Growth Factor Inhibition in Age-Related Macular Degeneration", Biodrugs, 2010, 24(3), pp. 183-194.

Nichols, "AAO: Ranibizumab (rhuRab) May Improve Vision in Age-Related Macular Degeneration", Doctor's Guide Global Edition, Nov. 24, 2003, www.pslgroup.com/dg/23f2aa.htm, DD, pp. 1-2.

Regeneron Pharmaceuticals Inc., "An Exploratory Study of the Safety, Tolerability and Biological Effect of a Single Intravitreal Administration of VEGF Trap in Patients with Diabetic Macular Edema", poster presented at the 2007 Association for Research in Vision and Ophthalmology meeting in Ft. Lauderdale, Florida, May 2007, pp. 1-3.

Regeneron Pharmaceuticals Inc., "Optical Coherence Tomography Outcomes of a Phase 1, Dose-Escalation, Safety, Tolerability, and Bioactivity Study of Intravitreal VEGF Trap in Patients with Neovascular Age-Related Macular Degeneration: The CLEAR-IT 1 Study" poster presented at the 2007 Association for Research in Vision and Ophthalmology meeting in Ft. Lauderdale, Florida, May 2007, pp. 1-2.

Regeneron Pharmaceuticals Inc., "VEGF Trap-Eye Final Phase 2 Results in Age-related Macular Degeneration Presented at 2008 Retina Society Meeting", Sep. 28, 2008, pp. 1-2.

FDA, "Highlights of Prescribing Information: Eylea", 2019, pp. 1-29.

(56) References Cited

OTHER PUBLICATIONS

Mitchell et al., "Ranibizumab (Lucentis) in neovascular age-related macular degeneration: evidence from clinical trials", Br J Ophthalmol, 2010, 94, pp. 2-13.
Massin, "Anti-VEGF Therapy for Diabetic Macular Edema: An Update", Retina Today, 2008, pp. 54-56.
Steinbrook, "The Price of Sight—Ranibizumab, Bevacizumab, and the Treatment of Macular Degeneration", N Engl J Med, 2006, 355(14), pp. 1409-1412.
Nei, "Age-Related Macular Degeneration What You Should Know", 2015, pp. 1-32.
Brown et al., "Anti-VEGF Agents in the Treatment of Neovascular Age-related Macular Degeneration: Applying Clinical Trial Results to the Treatment of Everyday Patients", Am J Ophthalmol, 2007, 144, pp. 627-637.
Nei, "Diabetic Retinopathy What You Should Know", 2015, pp. 1-20.
Ferrara et al., "Clinical applications of angiogenic growth factors and their inhibitors", Nature Medicine, 1999, 5(12), pp 1359-1364.
Ferrara et al., "Angiogenesis as a therapeutic target", Nature, 2005, 438, pp. 967-974.
FDA "Highlights of Prescribing Information", Lucentis, 2006, pp. 1-7.
Spielberg et al., "Intravitreal bevacizumab for myopic choroidal neovascularization: short-term and 1-year results", Bull Soc belge Ophtalmol, 2009, 312, 99 17-27.
Schmidt-Erfurth, "Current Concepts in the Management of Diabetic Macular Edema", Adv Stud Ophthalmol, 2010, 7(2), pp. 52-59.
Keane et al., "Effect of Ranibizumab retreatment frequency on neurosensory retinal volume in neovascular AMD", Retina, 2009, 29, pp. 592-600.
Anonymous, "VEGF Trap-Eye in Wet AMD CLEAR-IT 2: Summary of One-Year Key Results", Retina Society Meeting, 2008, Scottsdale, Arizona, pp. 1-29.
Regeneron, "VEGF Trap-Eye Final Phase 2 Results in Age-related Macular Degeneration Presented at 2008 Retina Society Meeting", 2008, pp. 1-2.
ARVO, "Winter/Spring Newsletter", 2008, pp. 1-20.
Retinal Physician, "Retinal Physician Symposium Covers Broad Range of Topics", 2006, pp. 1-8.
Nih, "A Study of rhuFab V2 (Ranibizumab) in Subjects With Subfoveal Choroidal Neovascularization Secondary to Age-Related Macular Degeneration (AMD)", ClinicalTrials.gov, 2021, pp. 1-7.
Shechtman et al., "A Look at CRUSIE and BRAVO", Review of Optometry, 2010, pp. 1-3.
Adamis, "Chapter 4: Ocular angiogenesis: vascular endothelial growth factor and other factors", Retinal Pharmacotherapy, 2010, pp. 23-36.
Ciulla et al., "Anti-vascular endothelial growth factor therapy for neovascular ocular diseases other than age-related macular degeneration", Curr Opin Ophthalmol, 2009, 20, pp. 166-174.
MPS Group, "Laser Photocoagulation of Subfoveal Neovascular Lesions in Age-Related Macular Degeneration", Arch Ophthalmol, 1991, 109, pp. 1220-1231.
Heier et al., "Ranibizumab for Macular Edema Due to Retinal Vein Occlusions", Ophthalmology, 2012, 119, pp. 802-809.
Benz et al., "CLEAR-IT-2: Interim Results Of The Phase II, Randomized, Controlled Dose-and Interval-ranging Study Of Repeated Intravitreal VEGF Trap Administration In Patients With Neovascular Age-related Macular Degeneration (AMO)", ARVO Annual Meeting Abstract, 2007, pp. 1-2.
Brown et al., "Sustained Benefits from Ranibizumab for Macular Edema Following Branch Retinal Vein Occlusion: 12-month outcomes of a Phase III Study", Ophthalmology, 2011, 118, pp. 1594-1602.
The Branch Vein Occlusion Study Group, "Argon laser photocoagulation for macular edema in branch vein occlusion", American Journal of Ophthalmology, 1984, 98(3), pp. 271-282.

Regillo et al., "Randomized, Double-Masked, Sham-Controlled Trial of Ranibizumab for Neovascular Age-related Macular Degeneration: PIER Study Year 1", Am J Ophthalmol, 2008, 145(2), pp. 239-248.
Fung, "An Optical Coherence Tomography-Guided, Variable Dosing Regimen with Intravitreal Ranibizumab (Lucentis) for Neovascular Age-related Macular Degeneration" Am J Ophthalmology, 2007, 143(4), pp. 566-583.
Nguyen et al., "Results of a Phase I, Dose-Escalation, Safety, Tolerability, and Bioactivity Study of Intravitreous VEGF Trap in Patients with Neovascular Age-Related Macular Degeneration", ARVO Annual Meeting Abstract, 2006, pp 1-2.
Bressler et al., "Photodynamic Therapy of Subfoveal Choroidal Neovascularization in Age-Related Macular Degeneration With Verteporfin", Arch Ophthalmol, 2001, 119, pp. 198-207.
Avery et al., "Intravitreal Bevacizumab (Avastin) for Neovascular Age-Related Macular Degeneration", Ophthalmology, 2006, 113, pp. 363-372.
Scott et al., "A Randomized Trial Comparing the Efficacy and Safety of Intravitreal Triamcinolone With Standard Care to Treat Vision Loss Associated With Macular Edema Secondary to Branch Retinal Vein Occlusion", Arch Ophthalmol, 2009, 127(9), pp. 1115-1128.
Nih, "History of Changes for Study: NCT00320775 Safety and Tolerability Study of Intravitreal VEGF-Trap Administration in Patients with neovascular AMD", ClinicalTrials.gov, 2015, pp. 1-5.
Clarkson et al., "Evaluation of Gird Pattern Photocoagulation for Macular Edema in Central Vein Occlusion", Ophthalmology, 1995, 102, pp. 1425-1433.
Rogers et al., "The Prevalence of Retinal Vein Occlusion: Pooled Data from Population Studies from the United States, Europe, Asia, and Australia", Ophthalmology, 2010, 117, pp. 313-319.
Schmidt-Erfurth et al., "Efficacy and Safety of Monthly versus Quarterly Ranibizumab Treatment in Neovascular Age-related Macular Degeneration: The EXCIE Study", Ophthalmology, 2011, 118(5), pp. 831-839.
Blodi et al., "A Randomized Trial Comparing the Efficacy and Safety of Intravitreal Triamcinolone With Observation to Treat Vision Loss Associated With Macular Edema Secondary to Central Retinal Vein Occlusion", Arch Ophthalmol, 2009, 127(9), pp. 1101-1114.
Rosenfeld et al., "Optical Coherence Tomography Findings After an Intravitreal Injection of Bevacizumab (Avastin) for Neovascular Age-Related Macular Degeneration", Ophthalmic Surg Lasers Imaging, 2005, 36, pp. 331-335.
Nguyen et al., "A Phase I Study of Intravitreal Vascular Endothelial Growth Factor Trap-Eye in Patients with Neovascular Age-Related Macular Degeneration", Ophthalmology, 2009. 116, 2141.
Dixon et al., "VEGF Trap-Eye for the Treatment of Neovascular Age-Related Macular Degeneration", Expert Opinion On Investigational Drugs. 2009, 18, 1573.
Adis, "Aflibercept AVE 0005, AVE 005, AVE0005, VEGF Trap-Regeneron, VEGF Trap (R1R2), VEGF Trap-Eye", Drugs R D, 2008, 9(4), pp. 261-269.
Semeraro et al., "Aflibercept in wet AMD: specific role and optimal use", Drug Design, Development and Therapy, 2013, 7, pp. 711-722.
Bayer, "Bayer HealthCare and Regeneron Announce Encouraging 32-week Follow-Up Results from Phase 2 Study of VEGF Trap-Eye in Age-related Macular Degeneration", Investor News 2008—Bayer Investor Relations, 2008, pp. 1-7.
Nih, "History of Changes for Study: NCT00509795 Vascular Endothelial Growth Factor (VEGF) Trap-Eye: Investigation of Efficacy and Safety in Wet AMD (VIEW 1)", ClinicalTrials.gov, 2012, pp. 1-27.
Nih, "History of Changes for Study: NCT00637377 VEGF Trap-Eye: Investigation of Efficacy and Safety in Wet AMD (VIEW 2)", ClinicalTrials.gov, 2014, pp. 1-20.
Heier, "Intravitreal VEGF Trap for AMD: An Update", Retina Today, 2009, pp. 44-45.
Engelbert et al., "Long-term follow-up for type 1 (subretinal pigment epithelium) neovascularization using a modified "treat and extend" dosing regimen of intravitreal antivascular endothelial growth factor therapy", Retina, 2010, 30, pp. 1368-1375.

(56) References Cited

OTHER PUBLICATIONS

Engelbert, "Treat and Extend' Dosing Of Intravitreal Antivascular Endothelial Growth Factor Therapy For Type 3 Neovascularization/Retinal Angiomatous Proliferation." Retina, 2009, 29(10), pp. 1424-1431.
Spaide et al., "Prospective Study of Intravitreal Ranibizumab as a Treatment for Decreased Visual Acuity Secondary to Central Retinal Vein Occlusion", Am J Ophthalmol, 2009, 147, 298-306.
Nih, "History of Changes for Study: NCT01012973 Vascular Endothelial Growth Factor (VEGF) Trap-Eye: Investigation of Efficacy and Safety in Central Retinal Vein Occlusion", ClinicalTrials.gov, 2014, pp. 1-14.
EyeTech Inc., "Macugen Label", 2008, pp. 1-3.
Bakri et al., "Intravitreal Silicone Oil Droplets After Intravitreal Drug Injections", Retina, 2008, 28, pp. 996-1001.
Csaky et al., "Safety Implications of Vascular Endothelial Growth Factor Blockade for Subjects Receiving Intravitreal Anti-Vascular Endothelial Growth Factor Therapies" Am J Ophthalmology, 2009, 148(5), pp. 647-656.
Honda et al., "Liposomes and nanotechnology in drug development: focus on ocular targets", International Journal of Nanomedicine, 2013, 8, pp. 495-504.
Rathore et al., "Characterization of Protein Rheology and Delivery Forces for Combination Products", Journal of Pharmaceutical Sciences, 2012, 101(12), pp. 4472-4480.
Penn et al., "Vascular Endothelial Growth Factor in Eye Disease", Prog Retin Eye Res, 2008, 27(4), pp. 331-371.
Wong, "Ocular Drug Delivery Systems: A rundown of methods for releasing drugs into the eye", Retina Today, 2016, pp 48-49.
Novartis, "Simulect", 1998, pp. 1-7.
Lalwani et al., "A Variable-dosing Regimen with Intravitreal Ranibizumab for Neovascular Age-related Macular Degeneration: Year 2 of the PrONTO Study", Am J Ophthalmol, 2009, 148, pp. 43-58.
Bashshur et al., "Intravitreal Bevacizumab for the Management of Choroidal Neovascularization in Age-related Macular Degeneration", Am J Ophthalmol, 2006, 142, pp. 1-9.
Holz et al., "VEGF Trap-Eye for macular oedema secondary to central retinal vein occlusion: 6-moth results of the phase III Galileo study", Br J Ophthalmol, 2013, 97, pp. 278-284.
Information from ClinicalTrials.gov archive History of Changes for Study: NCT00789477 "DME And VEGF Trap-Eye [Intravitreal Aflibercept Injection (IAI;EYLEA®;BAY86-5321 )] Investigation of Clinical Impact (Da Vinci)", Latest version submitted May 2, 2011 on ClinicalTrials.gov (NCT00789477 _2008-2011).
Information from ClinicalTrials.gov archive History of Changes for Study: NCT00789477 "DME And VEGF Trap-Eye [Intravitreal Aflibercept Injection (IAI;EYLEA®;BAY86-5321 )] Investigation of Clinical Impact (Da Vinci)", Latest version submitted Aug. 28, 2014 on ClinicalTrials.gov (NCT00789477 _2013-2014).
Information from ClinicalTrials.gov archive History of Changes for Study: NCT00943072 "Vascular Endothelial Growth Factor (VEGF) Trap-Eye: Investigation of Efficacy and Safety in Central Retinal Vein Occlusion (CRVO)", Latest version submitted May 9, 2011 on ClinicalTrials.gov (NCT00943072_2009-2011).
Information from ClinicalTrials.gov archive History of Changes for Study: NCT00943072 "Vascular Endothelial Growth Factor (VEGF) Trap-Eye: Investigation of Efficacy and Safety in Central Retinal Vein Occlusion (CRVO)", Latest version submitted Apr. 16, 2013 on ClinicalTrials.gov (NCT00943072_2012-2013).
Information from ClinicalTrials.gov archive View of NCT00637377 "Vascular Endothelial Growth Factor (VEGF) Trap- Eye: Investigation of Efficacy and Safety in Wet Age-Related Macular Degeneration (AMO) (VIEW 2)" ClinicalTrials.gov. Web. (Nov. 30, 2010).
Information from ClinicalTrials.gov archive on the VIEW 2 study (NCT00637377) "VEGF Trap-Eye: Investigation of Efficacy and Safety in Wet AMO (VIEW 2)" version available (updated on Mar. 17, 2008).
Information from ClinicalTrials.gov archive on the view of NCT00509795 "Vascular Endothelial Growth Factor (VEGF) Trap-Eye: Investigation of Efficacy and Safety in Wet Age-Related Macular Degeneration (AMO)" (Dec. 1, 2009).
Information from ClinicalTrials.gov archive on the view of NCT00789477 "DME and VEGF Trap-Eye: investigation of Clinical Impact" (Nov. 18, 2010).
Information from ClinicalTrials.gov archive on the view of NCT00509795 "Vascular Endothelial Growth Factor (VEGF) Trap-Eye: Investigation of Efficacy and Safety in Wet Age-Related Macular Degeneration (AMO)" (Jan. 7, 2011).
Information from ClinicalTrials.gov archive on the view of NCT01012973 Vascular Endothelial Growth Factor (VEGF) Trap-Eye: Investigation of Efficacy and Safety in Central Retinal Vein Occlusion (CRVO)(GALILEO), first posted Nov. 13, 2009; results first posted Nov. 22, 2012; last update posted Nov. 3, 2014; printed Dec. 4, 2019 (https://clinicaltrials gov/ct2/show/study/NCT01012973).
Karia, "Retinal vein occlusion: pathophysiology and treatment options", Clinical Ophthalmology, 2010, 4, pp. 809-816.
Korobelnik et al., "Intravitreal Aflibercept for Diabetic Macular Edema", Ophthalmology, 2014, 121(11), pp. 2247-2254.
Kuo et al., "Comparative evaluation of the antitumor activity of antiangiogenic proteins delivered by gene transfer", PNAS, 2001, 98(8), pp. 4605-4610.
Lalwani, "All About PrONTO: Study Yielded Good Results in AMO With Treatment Guided by OCT", Retina Today, 2007, pp. 1-6.
Major et al., "Da Vinci: DME and VEGF Trap-Eye: Investigation of Clinical Impact: Phase 2 Study in Patients with Diabetic Macular Edema (DME)", ARVO Annual Meeting Abstract, Apr. 2010, pp. 1-2.
Margolis et al., "Hemorrhagic Recurrence Of Neovascular Age-Related Macular Degeneration Not Predicted By Spectral Domain Optical Coherence Tomography", Retinal Cases & Brief Reports, 2010, 4, pp. 1-4.
Massin et al., "Safety and Efficacy of Ranibizumab in Diabetic Macular Edema (RESOLVE Study*)", Diabetes Care, 2010, 33(11), pp. 2399-2405.
Mitchell et al., "The RESTORE Study, Ranibizumab Monotherapy or Combined with Laser versus Laser Monotherapy for Diabetic Macular Edema", Ophthalmology, 2011, 188(4), pp. 615-625.
Nguyen et al., "A phase I trial of an IV-administered vascular endothelial growth factor trap for treatment in patients with choroidal neovascularization due to age-related macular degeneration", Ophthalmology, 2006, 113(9), pp. 1522e1-1522e14.
Nguyen et al., "Randomized, Double-masked, Active-controlled Phase 3 Trial of the Efficacy and Safety of Intravitreal VEGF Trap-Eye in Wet AMO: One-year Results of the VIEW 1 Study", ARVO Annual Meeting Abstract, Apr. 2011, pp. 1-2.
Nguyen et al., "Ranibizumab for Diabetic Macular Edema, Results from 2 Phase III Randomized Trials: Rise and Ride", Ophthalmology, 2012, 119(4), pp. 789-801.
Noguera-Troise et al., "Blockade of D114 inhibits tumour growth by promoting non-productive angiogenesis", Nature, 2006, 444, pp. 1032-1037.
Ohr et al., "Aflibercept in wet age-related macular degeneration: a perspective review", Ther Adv Chronic Dis, 2012, 3(4), pp. 153-161.
Olivera et al., "VEGF Trap R1 R2 suppresses experimental corneal angiogenesis", European Journal of Ophthalmology, 2010, 20(1), pp. 48-54.
Pai et al., "Current concepts in intravitreal drug therapy for diabetic retinopathy", Saudi Journal of Ophthalmology, 2010, 24(4), pp. 143-149.
Papadppoulos et al., "Binding and neutralization of vascular endothelial growth factor (VEGF) and related ligands by VEGF Trap, ranibizumab and bevacizumab", Angiogenesis, 2012, 15, pp. 171-185.
Regeneron SEC Form 10-K (Feb. 27, 2008).
Regeneron SEC Form 10-K (Feb. 26, 2009).
Regeneron SEC Form 10-K (Feb. 17, 2011).
Regeneron SEC Form 10-Q (May 8, 2006).
Regeneron SEC Form 10-Q (Aug. 8, 2006).

(56) References Cited

OTHER PUBLICATIONS

Regeneron SEC Form 10-Q (Nov. 6, 2006).
Regeneron SEC Form 10-Q (May 4, 2007).
Regeneron SEC Form 10-Q (Aug. 3, 2007).
Regeneron SEC Form 10-Q (Apr. 30, 2009).
Regeneron SEC Form 10-Q (Nov. 3, 2009).
Regeneron SEC Form 10-Q (Apr. 29, 2010).
Regeneron SEC Form 10-Q (Jul. 28, 2010).
Regeneron SEC Form 10-Q (Oct. 28, 2010).
Regeneron SEC Form 10-Q (May 3, 2011).
Regeneron SEC Form 10-Q (Jul. 28, 2011).
Regeneron SEC Form 10-Q (Oct. 27, 2011).
Regeneron SEC Form 8-K Exhibit: "Press Release of Regeneron Pharmaceuticals, Inc. dated May 1, 2006" (May 2, 2006).
Regeneron SEC Form 8-K Exhibit: "Press Release of Regeneron Pharmaceuticals, Inc. dated May 3, 2006" (May 5, 2006).
Information from ClinicalTrials.gov archive History of Changes for Study: NCT00320775 "Safety and Tolerability of Intravitreal Administration of VEGF Trap in Patients With Neovascular Age-Related Macular Degeneration", Latest version submitted Jun. 8, 2011 on ClinicalTrials.gov (NCT00320775 2006-2011).
Information from ClinicalTrials.gov archive History of Changes for Study: NCT00320775 "Safety and Tolerability of Intravitreal Administration of VEGF Trap in Patients With Neovascular Age-Related Macular Degeneration", Latest version submitted Mar. 16, 2015 on ClinicalTrials.gov (NCT00320775 2015).
Information from ClinicalTrials.gov archive History of Changes for Study: NCT00320788 "Safety and Efficacy of Repeated Intravitreal Administration of Vascular Endothelial Growth Factor (VEGF) Trap in Patients With Wet Age-Related Macular Degeneration (AMO)", Latest version submitted Dec. 1, 2011 on ClinicalTrials.gov (NCT00320788_2011).
Information from ClinicalTrials.gov archive History of Changes for Study: NCT00320788 "Safety and Efficacy of Repeated Intravitreal Administration of Vascular Endothelial Growth Factor (VEGF) Trap in Patients With Wet Age-Related Macular Degeneration (AMO)", Latest version submitted Jan. 27, 2012 on ClinicalTrials.gov (NCT00320788_2012).
Information from ClinicalTrials.gov archive History of Changes for Study: NCT00320814 "Phase 1 Study of VEGF Trap In Patients With Diabetic Macular Edema", Latest version submitted Jun. 8, 2011 on ClinicalTrials.gov (NCT00320814_2006-2011).
Information from ClinicalTrials.gov archive History of Changes for Study: NCT00509795 "Double-Masked Study of Efficacy and Safety of IVT VEGF Trap-Eye in Subjects With Wet AMO (VIEW 1 )", Latest version submitted Dec. 1, 2011 on ClinicalTrials.gov (NCT00509795_2007-2011).
Regeneron SEC Form 8-K Exhibit: "Slides presented at the Company's 2006 Annual Meeting of Shareholders held on Jun. 9, 2006" (Jun. 9, 2006).
Regeneron SEC Form 8-K Exhibit: "Press Release dated May 2, 2007" (May 3, 2007).
Regeneron SEC Form 8-K Exhibit: "Overheads for presentation at Regeneron's Annual Meeting of Shareholders to be held on Jun. 8, 2007" (Jun. 8, 2007).
Regeneron SEC Form 8-K Exhibit: "Press Release dated Oct. 1, 2007" (Oct. 1, 2007).
Regeneron SEC Form 8-K Exhibit: "Press Release dated Nov. 6, 2007" (Nov. 6, 2007).
Regeneron SEC Form 8-K Exhibit: "Press Release dated May 1, 2008" (May 2, 2008).
Zhou et al., "Regulation of angiogenesis and choroidal neovascularization by members of microRNA-23~25~24 clusters", PNAS, 2011, 108(20), pp. 8287-8292.
Schmidt-Erfurth et al. "Primary Results of an International Phase III Study Using Intravitreal VEGF Trap-Eye Compared to Ranibizumab in Patients with Wet AMO (VIEW 2)", ARVO Annual Meeting Abstract, Apr. 2011, pp. 1-2.

Schmidt-Erfurth et al., "Three-Year Outcomes of Individualized Ranibizumab Treatment in Patients with Diabetic Macular Edema", Ophthalmology, 2014, 121(5), pp. 1045-1053.
Schmidt-Erfurth et al., "Intravitreal Aflibercept Injection for Neovascular Age-related Macular Degeneration", Ophthalmology, 2014, 121, pp. 193-201.
Schnichels et al., "Comparative toxicity and proliferation testing of aflibercept, bevacizumab and ranibizumab on different ocular cells", Br J Ophthalmol, 2013, 97, pp. 917-923.
Semeraro et al., "Aflibercept in wet AMO: specific role and optimal use", Drug Design, Development and Therapy, 2013, 7, pp. 711-722.
Sharma et al., "Update on VEGF TRAP-Eye Clinical Trials and Retinal" Physician, 2010, pp. 1-6, URL: https://www.retinalphysician.com/issues/2010/nov-dec/update-on-vegf-trap-eye-clinical-trials.
Simo et al., "Advances in Medical Treatment of Diabetic Retinopathy", Diabetes Care, 2009, 32(8), pp. 1556-1562.
Slakter et al., "Influence of Baseline Angiographic Classification on Outcomes in the CLEAR-IT 2 Phase 2 Study of Intravitreal VEGF Trap-Eye in Neovascular Age-Related Macular Degeneration", ARVO Annual Meeting Abstract, Apr. 2010, pp. 1-2.
Slakter et al., "A Phase 2, Randomized, Controlled Dose-and Interval-Ranging Study of Intravitreal VEGF Trap-Eye In Patients with Neovascular Age-Related Macular Degeneration: Optical Coherence Tomography (OCT) and Fluorescein Angiography (FA) Outcomes at 1 Year", ARVO Annual Meeting Abstract, Apr. 2009, pp. 1-2.
Spaide, "Ranibizumab According to Need: A Treatment for Age-related Macular Degeneration" Am J Ophthalmology, 2007, 143(4), pp. 679-680.
Stewart, "The expanding role of vascular endothelial growth factor inhibitors in ophthalmology", Mayo Clin Proc, 2012, 87(1), pp. 77-88.
Stewart et al., "Predicted biological activity of intravitreal VEGF Trap", British Journal of Ophthalmology, 2008, 92(5), pp. 667-668.
Tannock et al., "Aflibercept versus placebo in combination with docetaxel and prednisone for treatment of men with metastatic castration-resistant prostate cancer (VENICE): a phase 3, double-blind randomized trial", Lancet Oncol, 2013, 14, pp. 760-768.
Thomas Reuters Integrity "VEGF Trap-Eye final phase II results in age-related macular degeneration presented at 2008 Retina Society Meeting", Sep. 28, 2008.
Thurston, "Complementary actions of VEGF and Angiopoietin-1 on blood vessel growth and leakage", J Anat, 2002, 200, pp. 575-580.
Thurston et al., "Vascular endothelial growth factor and other signaling pathways in developmental and pathologic angiogenesis", International Journal of Hematology, 2004, 80, pp. 7-20.
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO) (Galileo), Latest version submitted Oct. 27, 2014 on ClinicalTrials.gov (NCT01012973 01182013 27424.1).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO) (Galileo), Latest version submitted Oct. 27, 2014 on ClinicalTrials.gov (NCT01012973 01252011 27433.1).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO) (Galileo), Latest version submitted Oct. 27, 2014 on ClinicalTrials.gov (NCT01012973 01262012 27428.1).
Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO) (Galileo), Latest version submitted Oct. 27, 2014 on ClinicalTrials.gov (NCT01012973 01302013 27423.1).
Updated Information from ClinicalTrials.gov archive History of Changes for Study: NCT01012973 Vascular Endothelial Growth

(56) References Cited

OTHER PUBLICATIONS

Factor (VEGF) Trap-Eye: Investigation of Efficacy and Safety in Central Retinal Vein Occlusion (CRVO) (Galileo), Latest version submitted Oct. 27, 2014 on ClinicalTrials.gov (NCT01012973 02092010 27442.1).

Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO) (Galileo), Latest version submitted Oct. 27, 2014 on ClinicalTrials.gov (NCT01012973 02202012 27427.1).

Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO) (Galileo), Latest version submitted Oct. 27, 2014 on ClinicalTrials.gov (NCT01012973 03162010 27441.1).

Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO) (Galileo), Latest version submitted Oct. 27, 2014 on ClinicalTrials.gov (NCT01012973 04082011 27432.1).

Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO) (Galileo), Latest version submitted Oct. 27, 2014 on ClinicalTrials.gov (NCT01012973 04162010 27440.1).

Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO) (Galileo), Latest version submitted Oct. 27, 2014 on ClinicalTrials.gov (NCT01012973 06232011 27431.1).

Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO) (Galileo), Latest version submitted Oct. 27, 2014 on ClinicalTrials.gov (NCT01012973 07222010 27439.1).

Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO) (Galileo), Latest version submitted Oct. 27, 2014 on ClinicalTrials.gov NCT01012973 08252010 27438.1).

Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO) (Galileo), Latest version submitted Oct. 27, 2014 on ClinicalTrials.gov (NCT01012973 08262010 27437.1).

Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO) (Galileo), Latest version submitted Oct. 27, 2014 on ClinicalTrials.gov (NCT01012973 09082010 27436.1).

Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO) (Galileo), Latest version submitted Oct. 27, 2014 on ClinicalTrials.gov (NCT01012973 09192011 27430.1).

Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO) (Galileo), Latest version submitted Oct. 27, 2014 on ClinicalTrials.gov (NCT01012973 10042010 27435.1).

Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO) (Galileo), Latest version submitted Oct. 27, 2014 on ClinicalTrials.gov (NCT01012973 10232012 27426.1).

Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO) (Galileo), Latest version submitted Oct. 27, 2014 on ClinicalTrials.gov (NCT01012973 10272013 27422.1).

Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO)(Galileo), Latest version submitted Oct. 27, 2014 on ClinicalTrials.gov (NCT01012973 11012010 27434.1).

Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO) (Galileo), Latest version submitted Oct. 27, 2014 on ClinicalTrials.gov (NCT01012973 11132009 27 444.1).

Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO) (Galileo), Latest version submitted Oct. 27, 2014 on ClinicalTrials.gov (NCT01012973 11292011 27429.1).

Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO) (Galileo), Latest version submitted Oct. 27, 2014 on ClinicalTrials.gov (NCT01012973 12182012 27425.1).

Updated Information from ClinicalTrials.gov archive History of Changes for Study: NCT01012973 Vascular Endothelial Growth Factor (VEGF) Trap-Eye: Investigation of Efficacy and Safety in Central Retinal Vein Occlusion (CRVO) (Galileo), Latest version submitted Oct. 27, 2014 on ClinicalTrials.gov (NCT01012973 12212010 27443.1).

Wachsberger et al., "VEGF trap in combination with radiotherapy improves tumor control in u87 glioblastoma", Int J Radiation Oncology Biol Phys, 2007, 67(5), pp. 1526-1537.

Wolfson, "Regeneron Focuses on Age-Related Macular Degeneration", Chemistry & Biology, 2008, 15, pp. 303-304.

Kia et al., "Transgenic delivery of VEGF to mouse skin leads to an inflammatory condition resembling human psoriasis", Blood, 2003, 102(1), pp. 161-168.

Yancopoulos et al., "Vascular-specific growth factors and blood vessel formation", Nature, 2000, 407, pp. 242-248.

Yancopoulos, "Clinical Application of Therapies Targeting VEGF", Cell, 2010, 143, pp. 13-16.

Yung, "Moving Toward the Next Steps in Angiogenesis Therapy?", Society for Neuro-Oncology, 2008, 10, pp. 939.

Leys et al., "Neovascular growth following photodynamic therapy for choroidal hemangioma and neovascular regression after intravitreous injection of triamcinolone", Retina, 2006, 26(6), pp. 693-709.

Australian Government, Department of Health and Ageing, Australian Public Assessment Report for Aflibercept, 2012, pp 57-113.

Australian Government, Department of Health and Ageing, Australian Public Assessment Report for Aflibercept, 2012, pp 1-56.

Center for Drug Evaluation and Research, "Approved Labeling: Macugen", NDA 21-756, 2004, pp. 1-10.

Tian et al., "Association of genetic polymorphisms with response to bevacizumab for neovascular age-related macular degeneration in the Chinese population", Pharmacogenomics, 2012, 13(7), pp. 779-787.

(56) References Cited

OTHER PUBLICATIONS

Swaroop et al., "Genome Wide Association Study (GWAS) of Age-Related Macular Degeneration (AMD)", Investigative Ophthalmology & Visual Science, 2009, 50(13), 1614, pp. 1-2.
Smailhodzic "Cumulative Efect of Risk Alleles in CFH, ARMS2, and VEGFA on the Response to Ranibizumab Treatment in Age-related Macular Degeneration", Ophthalmology, 2012, 119(11), pp. 2304-2311.
Sharma et al., "Single Nucleotide Polymorphism and Serum Levels of VEGFR2 are Associated With Age Related Macular Degeneration", Current Neurovascular Research, 2012, 9(4), pp. 256-265.
Perlee et al., "Inclusion of Genotype with Fundus Phenotype Improves Accuracy of Predicting Choroidal Neovascularization and Geographic Atrophy", Ophthalmology, 2013, 120(9), pp. 1880-1892.
Park et al., "Pharmacogenetic associations with long-term response to antivascular endothelial growth factor treatment in neovascular AMD patients", Molecular Vision, 2014, 20, pp. 1680-1694.
Nischler et al., "Complement factor H Y402H gene polymorphism and response to intravitreal bevacizumab in exudative age- related macular degeneration", Acta Ophthalmologica, 2011, 89(4), pp. e344-e349.
SIMULECT Product Label dated May 1998, pp. 1-7.
Worakul et al., "Ocular pharmacokinetics/pharmacodynamics", European Journal of Pharmaceutics and Biopharmaceutics, 1997, 44(1627), pp. 71-83.
XOLAIR Product Label dated 2003, pp. 1-17.
Bird et al., "An International Classifcation and Grading System for Age-related Maculopathy and Age-related Macular Degeneration," Surv Ophthahnol, 1995, 39(5), pp. 367-374.
Bondy, "Recent Developments in Diagnosis and Care for Girls in Turner Syndrome," Advances in Endocrinology, 2014, pp. 1-9.
Chen et al., "Age-related Macular Degeneration: Genetic and Environmental Factors of Disease", Molecular Interventions, 2010, 10(5), pp. 217-281.
DeAngelis et al., "Genetics of Age-Related Macular Degeneration Current Concepts, Future Directions," Semin Ophthalmol, 2011, 26(3), pp. 77-93.
Eylea Canadian Product Monograph dated Sep. 9, 2021, pp. 1-69.
Eylea U.S. Label dated 2021-11, pp. 1-15.
Heier, "Intravitreal Afibercept for AMD: 2-year Results", Retina Today, Mar. 2012, pp. 49-51.
Hermann et al., "Variants in the VEGFA gene and visual outcome after anti-VEGF treatment for neovascular age-related macular degeneration", Investigative Ophthalmology & Visual Science, 2013, 54, 4120, pp. 1-2.
McKibbin et al., "CFH, VEGF and HTRA1 promoter genotype may influence the response to intravitreal ranibizumab therapy for neovascular age-related macular degeneration", British Journal of Ophthalmology, 2012, 96(2), pp. 208-212.
Rosenfeld, "My Use of Afibercept in Clinical Practice", Retina Today, Mar. 2012, p. 50.
Thomas et al., "Comparative effectiveness of afibercept for the treatment of patients with neovascular age-related macular degeneration", Clinical Ophthalmology, 2013, 7, pp. 495-501.
Abedi et al., "Genetic Influences on the Outcome of Anti-Vascular Endothelial Growth Factor Treatment in Neovascular Age-related Macular Degeneration", Ophthalmology, 2013, 120(8), pp. 1641-1648.
Andreoli et al., "Comprehensive Analysis of CFH and LOC387715/ARMS2/HTRAI Variants with respect to Phenotype in Advanced Age Related Macular Degeneration", American Journal of Ophthalmology, 2009, 148(6), pp. 869-874.
Barral et al., "Expanded Genome Scan in Extended Families with Age-Related Macular Degeneration", Investigative Ophthalmology & Visual Science, 2006, 47(12), pp. 5453-5459.
Bulgu et al., "Vascular endothelial growth factor gene polymorphisms in age-related macular degeneration in a Turkish population", International Journal of Ophthalmology, 2014, 7(5), pp. 773-777.

Chen et al., "Association between Variant Y402H in Age-Related Macular Degeneration (AMD) Susceptibility Gene CFH and Treatment Response of AMD: A Meta-Analysis", PLOS ONE, 2012, 7(8), pp. e42464.
Dewan et al., "HTRAI Promoter Polymorphism in Wet Age-Related Macular Degeneration", Science, 2006, 314, pp. 989-992.
Veloso et al., "VEGF Gene Polymorphism and Response to Intravitreal Ranibizumab in Neovascular Age-Related Macular Degeneration", Ophthalmic Research, 2013, 51(1), pp. 1-8.
Regeneron SEC Form 8-K Exhibit: "Press Release dated Nov. 4, 2008" (Nov. 4, 2008).
Regeneron SEC Form 8-K Exhibit: "99(a) Slides that Regeneron Pharmaceuticals, Inc. intends to use in conjunction with meetings with investors at the J.P. Morgan 27th Annual Healthcare Conference in San Francisco on Jan. 12-15, 2009." (Jan. 9, 2009).
Regeneron SEC Form 8-K Exhibit: "Press Release dated Apr. 30, 2009" (May 1, 2009).
Regeneron SEC Form 8-K Exhibit: "Press Release dated Nov. 3, 2009." (Nov. 4, 2009).
Regeneron SEC Form 8-K Exhibit: "Press Release Reporting Positive Results for VEGF Trap-Eye in Phase 3 Study in Central Retinal Vein Occlusion (CRVO) and in Phase 2 Study in Diabetic Macular Edema (DME) dated Dec. 20, 201 O." (Dec. 20, 2010).
Regeneron SEC Form 8-K Exhibit: "Press Release dated Feb. 17, 2011" (Feb. 18, 2011).
Regeneron SEC Form 8-K Exhibit: "Press Release Reporting Positive Results for VEGF Trap-Eye in Second Phase 3 Study in Central Retinal Vein Occlusion, dated Apr. 27, 2011" (Apr. 27, 2011).
Regeneron SEC Form 8-K Exhibit: "Press Release dated May 3, 2011." (May 3, 2011).
Regeneron SEC Form 8-K Exhibit: "Press Release, dated Jun. 17, 2011, Announcing that EYLEATM (aflibercept ophthalmic solution) Received Unanimous Recommendation for Approval for Treatment of Wet AMO from FDA Advisory Committee." (Jun. 21, 2011).
Regeneron SEC Form 8-K Exhibit: "Presentation entitled VEGF Trap-Eye in CRVO: 1-year Results of the Phase 3 Copernicus Study" (Aug. 22, 2011).
Regeneron SEC Form 8-K Exhibit: "Press Release Announcing FDA Approval of EYLEA™ (aflibercept) Injection for the Treatment of Wet Age-Related Macular Degeneration, dated Nov. 18, 2011" (Nov. 21, 2011).
Regeneron Press Release "Positive Interim Phase 2 Data Reported For VEGF Trap-Eye In Age-Related Macular Degeneration" (Mar. 27, 2007).
Regeneron Press Release "VEGF TRAP-Eye Phase 2 Wet AMO Results Reported At Arvo Annual Meeting" (May 9, 2007).
Regeneron Press Release "Regeneron Reports Second Quarter Financial And Operating Results" (Aug. 1, 2007).
Regeneron Pharmaceuticals, Inc., "Regeneron and Bayer Healthcare Initiate Phase 3 Global Development Program for VEGF Trap-Eye In Wet Age-Related Macular Degeneration (AMO)" (Aug. 2, 2007).
Regeneron Pharmaceuticals, Inc. Form 10-Q, published on Nov. 7, 2007 for the period ending Sep. 30, 2007.
Regeneron Press Release "Regeneron Announces Positive Primary Endpoint Results From A Phase 2 Study Of VEGF Trap-Eye In Age-Related Macular Degeneration" (Oct. 1, 2007).
Regeneron Press Release "Regeneron Reports Fourth Quarter And Full Year 2007 Financial And Operating Results" (Feb. 27, 2008).
Regeneron Pharmaceuticals, Inc., "Regeneron and Bayer HealthCare Announce Encouraging 32-Week Follow-up Results from a Phase 2 Study of VEGF Trap-Eye in Age-Related Macular Degeneration" (Apr. 28, 2008).
Regeneron, Press release "Regeneron Reports First Quarter 2008 Financial and Operating Results", May 1, 2008.
Regeneron Press Release, "Bayer and Regeneron Dose First Patient in Second Phase 3 Study for VEGF Trap-Eye in Wet Age-Related Macular Degeneration." May 8, 2008.
Regeneron Pharmaceuticals, Inc., "Regeneron and Bayer HealthCare Announce VEGF Trap-Eye Achieved Durable Improvement in Vision over 52 Weeks in a Phase 2 Study in Patients with Age-related Macular Degeneration" (Aug. 19, 2008).

(56) References Cited

OTHER PUBLICATIONS

Regeneron Pharmaceuticals Inc.,"VIEW 1 Vascular Endothelial Growth Factor (VEGF) Trap-Eye 1-Year Results: Investigation of Efficacy and Safety in Wet Age-Related Macular Degeneration (AMO)" presented at Bascom Palmer Eye Institute's Angiogenesis, Exudation and Degeneration 2011 meeting in Miami, Florida (Feb. 12, 2011).

Regeneron Pharmaceuticals Inc.,"VIEW 2 Vascular Endothelial Growth Factor (VEGF) Trap-Eye 1-Year Results: Investigation of Efficacy and Safety in Wet Age-Related Macular Degeneration (AMO)" presented at Bascom Palmer Eye Institute's Angiogenesis, Exudation and Degeneration 2011 meeting in Miami, Florida (Feb. 12, 2011).

Regeneron Pharmaceuticals Inc., "VEGF Trap-Eye CLEAR-IT 2 Final Primary Endpoint Results" presented at the 2007 Retina Society Conference in Boston, Massachusetts (Sep. 30, 2007).

Regeneron 2008 Annual Report.

Regeneron Pharmaceuticals, Inc. "Regeneron Reports Full Year and Fourth Quarter 2008 Financial and Operating Results" (Feb. 26, 2009).

Regeneron Pharmaceuticals, Inc. "Bayer and Regeneron Extend Development Program for VEGF Trap-Eye to Include Central Retinal Vein Occlusion" (Apr. 30, 2009).

Regeneron Press Release "First Patient Enrolled In Regeneron And Bayer Healthcare VEGF Trap-Eye Phase 3 Program In Central Retinal Vein Occlusion" (Jul. 23, 2009).

Regeneron Press Release "Enrollment Completed in Regeneron and Bayer HealthCare Phase 3 Studies of VEGF Trap-Eye in Neovascular Age-Related Macular Degeneration (Wet AMO)" Sep. 14, 2009.

Regeneron 2009 Annual Report and 10-K.

Regeneron Press Release, "VEGF Trap-Eye Shows Positive Results in a Phase 2 Study in Patients With Diabetic Macular Edema." Feb. 18, 2010.

Regeneron Press Release "Regeneron Schedules Nov. 22, 2010 Teleconference And Webcast To Discuss Results Of Two Phase 3 Studies With VEGF Trap-Eye In Wet Age-Related Macular Degeneration" (Nov. 19, 2010).

Regeneron Press Release "Bayer and Regeneron Report Positive Top-Line Results of Two Phase 3 Studies with VEGF Trap-Eye in Wet Age-related Macular Degeneration" Nov. 22, 2010.

Regeneron Press Release "Regeneron and Bayer Report Positive Results for VEGF Trap-Eye in Phase 3 Study in Central Retinal Vein Occlusion (CRVO) and in Phase 2 Study in Diabetic Macular Edema (DME)" Dec. 20, 2010.

Regeneron 2010 Annual Report and 10-K.

Regeneron Press Release "Regeneron And Bayer Start Phase 3 Trial To Extend Ophthalmology Research & Development Program For VEGF Trap-Eye In Asia" (Jan. 18, 2011).

Regeneron Press Release "Regeneron To Webcast Investor Briefing On VEGF Trap-Eye Clinical Program On Sunday, February 13th At 9 Am Et" (Feb. 9, 2011).

Regeneron Press Release "Regeneron Submits Biologics License Application To FDA For VEGF Trap-Eye For Treatment Of Wet Age-Related Macular Degeneration" (Feb. 22, 2011).

Regeneron Press Release "Regeneron And Bayer Announce Start Of Phase 3 Clinical Program In Diabetic Macular Edema" (Apr. 8, 2011).

Regeneron Pharmaceuticals, Inc., "FDA Grants Priority Review for VEGF Trap-Eye for the Treatment of Wet Age-Related Macular Degeneration" (Apr. 18, 2011).

Regeneron Press Release VEGF Trap-Eye Submitted for EU Marketing Authorization for Treatment of Wet Age-Related Macular Degeneration (Jun. 7, 2011).

Regeneron Pharmaceuticals, Inc., "Regeneron Announces EYLEA TM (aflibercept ophthalmic solution) Receives Unanimous Recommendation for Approval for Treatment of Wet AMO from FDA Advisory Committee" (Jun. 17, 2011).

Regeneron Press Release "Regeneron Announces Clinical Presentations at ASRS 2011 Annual Meeting" (Aug. 17, 2011).

Regeneron Pharmaceuticals, Inc., Regeneron Announces FDA Approval of EYLEA&153 (aflibercept) Injection for the Treatment of Wet Age-Related Macular Degeneration: Corrected (Nov. 18, 2011).

Regeneron Pharmaceuticals, Inc., "Regeneron and Bayer Initiate Phase 3 Clinical Program for the Treatment of Wet Age-Related Macular Degeneration in China" (Nov. 28, 2011).

Regeneron Pharmaceuticals, Inc., "Two Year Results of Phase 3 Studies with EYLEA TM (aflibercept) Injection in wet AMO Show Sustained Improvement in Visual Acuity" (Dec. 5, 2011).

Rosenfeld, "Lessons Learned From Avastin and OCT-The Great, the Good, the Bad, and the Ugly: The LXXV Edward Jackson Memorial Lecture", Am J Ophthalmology, 2019, 204, pp. 26-45.

Rudge et al., "VEGF Trap complex formation measures production rates of VEGF, providing a biomarker for predicting efficacious angiogenic blockade", PNAS, 2007, 104(47), pp. 18363-18370.

Rudge et al., "Clinical Development of VEGF Trap", In: Figg W.D., Folkman J. (eds) Angiogenesis, 2008, Chapter 36, pp 415-420.

ARVO, "Summer Newsletter", 2007, pp. 1-28.

Korobelnik et al., "Intravitreal Aflibercept Injection for Macular Edema Resulting from Central Retinal Vein Occlusion", Ophthalmology, 2014, 121, pp. 202-208.

Reichert, "Antibody-based therapeutics to watch in 2011", mAbs, 2011, 3(1), pp. 76-99.

Anderson et al., "Delivery of anti-angiogenic molecular therapies for retinal disease", Drug Discovery Today, 2010, 15(7/8), pp. 272-282.

Ni et al., "Emerging Pharmacologic Therapies for Wet Age-Related Macular Degeneration", Ophthalmologica, 2009, 223, pp. 401-410.

Zarbin et al., "Pathway-based Therapies For Age-related Macular Degeneration", Retina, 2010, 30, pp. 1350-1367.

Kim et al., "Potent VEGF blockade causes regression of coopted vessels in a model of neuroblastoma", PNAS, 2002, 99(17), pp. 11399-11404.

Shihua, "China's Kanghong Pharma Hits Limit Down as France Stops Trials of Ophthalmic Drug", Yicai Global, 2021, op 1-3.

Notice of Allowance dated Jul. 26. 2023 in related U.S. Appl. No. 15/995,518.

Daniels et al., "Chapter 4: Choroidal Neovascularization: VEGF Pathways", in Age-Related Macular Degeneration, 2013, 3rd ed, Baton Raton: CRC Press, pp. 45-53.

Yannuzzi et al., "Use of indocyanine green angiography in the management of age-related macular degeneration", in Age-Related Macular Degeneration, 2013, 3rd ed, Baton Raton: CRC Press, pp. 173-187.

Bui et al., "Chapter 23: Photodynamic therapy for neovascular age-related macular degeneration", in Age-Related Macular Degeneration, 2013, 3rd ed, Baton Raton: CRC Press, pp. 279-287.

Chow et al., "Chapter 19: Anti-VEGF drugs and clinical trials" in Age-Related Macular Degeneration, 2013, 3rd ed, Baton Raton: CRC Press, pp. 229-242.

Freund et al., "Treat-and-extend regimens with anti-VEGF agents in retinal diseases: A literature Review and Consensus Recommendations", Retina, 2015, 35(8), pp. 1489-1506.

Bolton et al., "Pharmaceutical Statistics: Practical and Clinical Applications", 2004, 4th ed, New York: Marcel Dekker, pp. 108-113.

Hong et al., "Sample Size and Statical Power Calculation in Genetic Association Studies", Genomics & Informatics, 2012, 10(2), pp. 117-122.

Clinicaltrials.gov, "Vascular Endothelial Growth Factor VEGF Trap-Eye: Investigation of Efficacy and Safety in Wet Age-Related Macular Degeneration (AMD) (VIEW1)", updated Dec. 28, 2012, online: National Library of Medicine <https://clinicaltrials.gov/study/NCT00509795>, pp. 1-41.

Clinicaltrials.gov, "Vascular Endothelial Growth Factor VEGF Trap-Eye: Investigation of Efficacy and Safety in Wet Age-Related Macular Degeneration (Amd) (VIEW2)", updated Dec. 12, 2014, online: National Library of Medicine <https://clinicaltrials.gov/study/NCT00637377>, pp. 1-50.

Hagstrom et al., "Pharmacogenetics for Genes Associated with Age-Related Macular Degeneration in the Comparison of AMD Treatments Trials (CATT)", Ophthalmology, 2013, 120, pp. 593-599.

| | VIEW 1 | VIEW 1 PGx |
|---|---|---|
| n (full analysis set) | 1210 | 362 |
| Completed study, n (%) | 1174 (96.6%) | 320 (88.2%) |
| Women, n (%) | 711 (58.8%) | 203 (56.1%) |
| White, n (%) | 1169 (96.6%) | 352 (97.2%) |
| Mean age, years (SD) | 78.1 (8.0) | 77.8 (7.8) |
| BCVA, letters (SD) | 55.1 (13.1) | 55.5 (12.9) |
| CRT, μm (SD) | 316.6 (107.2) | 312.9 (108.7) |
| Baseline CNV area, mm² (SD) | 6.6 (5.0) | 6.10 (4.7) |
| Baseline Type of CNV, n (%) | | |
| Occult | 464 (38.3%) | 129 (35.6%) |
| Minimally Classic | 424 (35.0%) | 129 (35.6%) |
| Predominantly | 311 (25.7%) | 101 (27.9%) |
| Missing/Other | 11 (<0.1%) | 3 (0.8%) |

Figure 2

| Phenotype | POS | CHR | Closest Gene | SNP | N | OR | P | REF |
|---|---|---|---|---|---|---|---|---|
| Gain 15 Letters | 140765 | 3 | MECOM-004 | rs2106124 | 301 | 2.471 | 9.51E-06 | A |
| Gain 15 Letters | 140766 | 3 | MECOM-004 | rs1879796 | 301 | 2.477 | 9.20E-06 | T |
| Gain 15 Letters | 528346 | 15 | NTRK3 | rs12148845 | 301 | 2.621 | 4.88E-06 | G |
| Gain 15 Letters | 528351 | 15 | NTRK3 | rs12148100 | 301 | 2.587 | 7.15E-06 | T |
| Presence Retinal Fluid | 641343 | 23 | PRKX | rs20566088 | 271 | 0.2578 | 7.27E-07 | A |
| Presence Retinal Fluid | 641345 | 23 | PRKX | rs59620084 | 271 | 0.3461 | 8.59E-06 | G |
| Presence Retinal Fluid | 641347 | 23 | PRKX | rs59620087 | 271 | 0.3151 | 5.48E-06 | A |
| Presence Retinal Fluid | 641349 | 23 | PRKX | rs5915722 | 271 | 0.3406 | 7.38E-06 | C |
| Presence Retinal Fluid | 641353 | 23 | PRKX | rs5963095 | 271 | 0.3461 | 8.59E-06 | C |
| Injections > 7 | 168932 | 4 | ANK2 | rs174482885 | 305 | 3.808 | 5.03E-06 | G |
| Injections > 7 | 168950 | 4 | ANK2 | rs17629019 | 305 | 3.575 | 9.36E-06 | A |

Figure 8

METHODS OF ASSOCIATING GENETIC VARIANTS WITH A CLINICAL OUTCOME IN PATIENTS SUFFERING FROM AGE-RELATED MACULAR DEGENERATION TREATED WITH ANTI-VEGF

FIELD

The present disclosure is directed, in part, to methods and compositions for associating a genetic variant with visual acuity and anatomic outcomes, and treatment of macular degeneration patients.

BACKGROUND

Macular degeneration is a serious medical condition, in which intraretinal fluid builds up and can damage the retina, resulting in loss of vision in the center of the visual field. Macular degeneration can be age-related. "Dry" (nonexudative") and "wet" ("neovascular" or "exudative") forms of macular degeneration have been recognized.

In neovascular macular degeneration, vision loss can be due to abnormal blood vessel growth (choroidal neovascularization). Proliferation of abnormal blood vessels in the retina is stimulated by vascular endothelial growth factor (VEGF). The new vessels are fragile, and can lead to blood and protein leakage below the macula. Bleeding, leaking, and scarring from those blood vessels can eventually cause irreversible damage to the photoreceptors and rapid vision loss.

EYLEA® (aflibercept) injection and Lucentis© (ranibizumab) are biologic drugs that havebeen approved in the United States and Europe for the treatment of wet macular degeneration. Aflibercept and ranibizumab are VEGF inhibitors.

SUMMARY

Disclosed herein are methods of associating a genetic variant with visual acuity, anatomic outcomes or treatment frequency, the method comprising: statistically associating (i) one or more genetic variants in a population of neovascular age-related macular degeneration subjects who have been administered aflibercept or ranibizumab with (ii) an anatomical outcome in the same population of neovascular age-related macular degeneration subjects.

Disclosed herein are methods of associating a genetic variant with visual acuity, anatomic outcomes or treatment frequency, the method comprising: (a) statistically associating (i) one or more genetic variants in a population of neovascular age-related macular degeneration subjects who have been administered an intravitreal anti-VEGF agent with (ii) an anatomical outcome in the same population of neovascular age-related macular degeneration subjects, wherein one or more genetic variants is associated with a the presence of intraretinal cystoid edema (fluid), compared to the absence of intraretinal cystoid edema (fluid) after one year of treatment.

Disclosed herein are methods of associating a genetic variant with intraretinal fluid, the method comprising: statistically associating (a) one or more genetic variants in a population of neovascular age-related macular degeneration subjects with (b) intraretinal fluid in the same population of neovascular age-related macular degeneration subjects, wherein the one or more genetic variants is associated with a lower level of intraretinal fluid in neovascular age-related macular degeneration subjects treated with an intravitreal anti-VEGF agent and who have one or two copies of the genetic variant allele, compared to the level of intraretinal fluid in neovascular age-related macular degeneration subjects treated with an intravitreal anti-VEGF agent and who do not have a copy of the genetic variant allele.

Disclosed herein are methods for treating a macular degeneration patient with a vascular endothelial growth factor (VEGF) inhibitor, comprising the steps of: determining whether the patient has one or more genetic variants associated with visual acuity and/or anatomic outcome by: performing or having performed a genotype assay on a DNA sample obtained from the patient to determine if the patient has one or more genetic variants associated with visual acuity and/or anatomic outcome; and when the patient has one or more of the genetic variants associated with improved visual acuity and/or anatomic outcome, and when the patient exhibits improved visual acuity and/or anatomic outcome after about one year of administering the VEGF inhibitor to the patient, modifying the dosing frequency of administering about 2 mg of the VEGF inhibitor to the patient from about every 8 weeks to about every 9 to 12 weeks to the patient; or when the patient does not have one or more of the genetic variants associated with improved visual acuity and/or anatomic outcome, and when the patient does not exhibit improved visual acuity and/or anatomic outcome after about one year of administering the VEGF inhibitor to the patient, modifying the dosing frequency of administering about 2 mg of the VEGF inhibitor to the patient from about every 8 weeks to about every 4 to 6 weeks to the patient.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 2 shows baseline characteristics and clinical demographics of a PGx Substudy including gender, age, race, visual acuity and lesion type that were reflective of distributions observed in the VIEW 1 full analysis set.

FIG. 8 shows the SNPs identified in the study of the examples herein.

DETAILED DESCRIPTION

Figure 1:
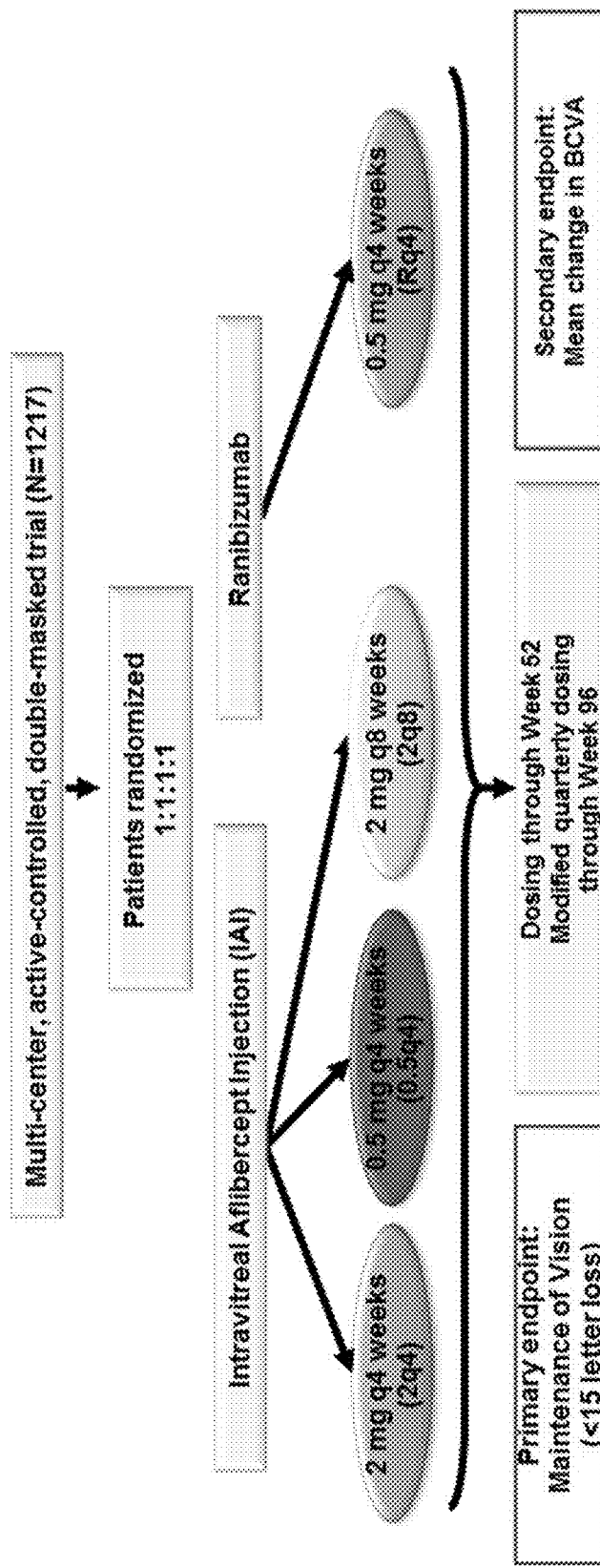
FIG. 1 shows an overview of a statistical study used to identify genetic variants associated with anti-VEGF drug response as measured by visual acuity, anatomic outcomes and treatment frequency in the VIEW 1 study.

The disclosed method and compositions may be understood more readily by reference to the following detailed description of particular embodiments and the Example included therein and to the Figures and their previous and following description.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

It is understood that the disclosed methods and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a PRR antagonist is disclosed and discussed and a number of modifications that can be made are discussed, each and every combination and permutation of the PRR antagonist and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values described herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that throughout the application, data are provided in a number of different formats, and that these data, represent endpoints, starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units is also disclosed. For example, if 10 and 15 are disclosed, then 11, 12, 13, and 14 are also disclosed.

"Optional" or "optionally" means that the subsequently described event or circumstance may or may not occur and that the description includes instances where said event or circumstance occurs and instances where it does not.

The word "or" as used herein means any one member of a particular list and also includes any combination of members of that list.

As used herein, the term "subject" means an individual. In one aspect, a subject is a mammal such as a human. In one aspect a subject can be a non-human primate. Non-human primates include marmosets, monkeys, chimpanzees, gorillas, orangutans, and gibbons, to name a few. The term "subject" also includes domesticated animals, such as cats, dogs, etc., livestock (for example, cattle (cows), horses, pigs, sheep, goats, etc.), laboratory animals (for example, ferret, chinchilla, mouse, rabbit, rat, gerbil, guinea pig, etc.) and avian species (for example, chickens, turkeys, ducks, pheasants, pigeons, doves, parrots, cockatoos, geese, etc.). Subjects can also include, but are not limited to fish (for example, zebrafish, goldfish, tilapia, salmon, and trout), amphibians and reptiles. As used herein, a "subject" is the same as a "patient," and the terms can be used interchangeably.

The term "polymorphism" refers to the occurrence of one or more genetically determined alternative sequences or alleles in a population. A "polymorphic site" is the locus at which sequence divergence occurs. Polymorphic sites have at least one allele. A diallelic polymorphism has two alleles. A triallelic polymorphism has three alleles. Diploid organisms may be homozygous or heterozygous for allelic forms. A polymorphic site can be as small as one base pair. Examples of polymorphic sites include: restriction fragment length polymorphisms (RFLPs), variable number of tandem repeats (VNTRs), hypervariable regions, minisatellites, dinucleotide repeats, trinucleotide repeats, tetranucleotide repeats, and simple sequence repeats. As used herein, reference to a "polymorphism" can encompass a set of polymorphisms (i.e., a haplotype).

A "single nucleotide polymorphism (SNP)" can occur at a polymorphic site occupied by a single nucleotide, which is the site of variation between allelic sequences. The site can be preceded by and followed by highly conserved sequences of the allele. A SNP can arise due to substitution of one nucleotide for another at the polymorphic site. Replacement of one purine by another purine or one pyrimidine by another pyrimidine is called a transition. Replacement of a purine by a pyrimidine or vice versa is called a transversion. A synonymous SNP refers to a substitution of one nucleotide for another in the coding region that does not change the amino acid sequence of the encoded polypeptide. A non-synonymous SNP refers to a substitution of one nucleotide for another in the coding region that changes the amino acid sequence of the encoded polypeptide. A SNP may also arise from a deletion or an insertion of a nucleotide or nucleotides relative to a reference allele.

A "set" of polymorphisms means one or more polymorphism, e.g., at least 1, at least 2, at least 3, at least 4, at least 5, at least 6, or more than 6 polymorphisms.

As used herein, a "nucleic acid," "polynucleotide," or "oligonucleotide" can be a polymeric form of nucleotides of any length, can be DNA or RNA, and can be single- or double-stranded. Nucleic acids can include promoters or other regulatory sequences. Oligonucleotides can be prepared by synthetic means. Nucleic acids include segments of DNA, or their complements spanning or flanking any one of the polymorphic sites. The segments can be between 5 and 100 contiguous bases and can range from a lower limit of 5, 10, 15, 20, or 25 nucleotides to an upper limit of 10, 15, 20, 25, 30, 50, or 100 nucleotides (where the upper limit is greater than the lower limit). Nucleic acids between 5-10, 5-20, 10-20, 12-30, 15-30, 10-50, 20-50, or 20-100 bases are common. The polymorphic site can occur within any position of the segment. A reference to the sequence of one strand of a double-stranded nucleic acid defines the complementary sequence and except where otherwise clear from context, a reference to one strand of a nucleic acid also refers to its complement.

"Nucleotide" as described herein refers to molecules that, when joined, make up the individual structural units of the nucleic acids RNA and DNA. A nucleotide is composed of a nucleobase (nitrogenous base), a five-carbon sugar (either ribose or 2-deoxyribose), and one phosphate group. "Nucleic acids" are polymeric macromolecules made from nucleotide monomers. In DNA, the purine bases are adenine (A) and guanine (G), while the pyrimidines are thymine (T) and cytosine (C). RNA uses uracil (U) in place of thymine (T).

As used herein, the term "genetic variant" or "variant" refers to a nucleotide sequence in which the sequence differs from the sequence most prevalent in a population, for example by one nucleotide, in the case of the SNPs described herein. For example, some variations or substitutions in a nucleotide sequence alter a codon so that a different amino acid is encoded resulting in a genetic variant polypeptide. Other non-limiting examples of genetic variants include, insertions, deletions, indels, frameshift variants, stop codon variants, synonymous variants, non-synonymous variants and copy number variants (e.g., deletions and duplications). The term "genetic variant," can also refer to a polypeptide in which the sequence differs from the sequence most prevalent in a population at a position that does not change the amino acid sequence of the encoded polypeptide (i.e., a conserved change). Genetic variant polypeptides can be encoded by a risk haplotype, encoded by a protective haplotype, or can be encoded by a neutral haplotype. Genetic variant polypeptides can be associated with risk, associated with protection, or can be neutral.

By "isolated nucleic acid" or "purified nucleic acid" is meant DNA that is free of the genes that, in the naturally-occurring genome of the organism from which the DNA of the invention is derived, flank the gene. The term therefore includes, for example, a recombinant DNA which is incorporated into a vector, such as an autonomously replicating plasmid or virus; or incorporated into the genomic DNA of a prokaryote or eukaryote (e.g., a transgene); or which exists as a separate molecule (for example, a cDNA or a genomic or cDNA fragment produced by PCR, restriction endonuclease digestion, or chemical or in vitro synthesis). It also includes a recombinant DNA which is part of a hybrid gene encoding additional polypeptide sequence. The term "isolated nucleic acid" also refers to RNA, e.g., an mRNA molecule that is encoded by an isolated DNA molecule, or that is chemically synthesized, or that is separated or substantially free from at least some cellular components, for example, other types of RNA molecules or polypeptide molecules.

As used herein, "treated" or "treating" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii)

inhibiting the disease, i.e., arresting its development; or (iii) relieving the disease, i.e., causing regression of the disease.

The terms "administering", "administered" and "administration" refer to any method of providing a pharmaceutical preparation to a subject. Such methods are well known to those skilled in the art and include, but are not limited to, oral administration, sublingual administration, trans-buccal mucosa administration, transdermal administration, administration by inhalation, nasal administration, topical administration, intravaginal administration, ophthalmic administration, intraaural administration, intracerebral administration, intrathecal administration, rectal administration, intraperitoneal administration, and parenteral administration, including injectable such as intravenous administration, intra-arterial administration, intramuscular administration, intradermal administration, and subcutaneous administration. Ophthalmic administration can include topical administration, subconjunctival administration, sub-Tenon's administration, epibulbar administration, retrobulbar administration, intra-orbital administration, and intraocular administration, which includes intra-vitreal administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

Calculations of sequence similarity or sequence identity between sequences (the terms are used interchangeably herein) are performed as follows. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch, (1970, J. Mol. Biol. 48: 444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna. CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller (1989, Cabios, 4: 11-17) which has been incorporated into the ALIGN program (version 2.0), using a PAM120 weight residue table, a gap length penalty of 12 and a gap penalty of 4.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Those skilled in the art will recognize, or be able to ascertain using no more than routine experimentation, many equivalents to the specific embodiments of the method and compositions described herein. Such equivalents are intended to be encompassed by the following claims.

Methods

Disclosed herein are methods of associating a genetic variant with visual acuity, anatomic outcomes or treatment frequency, the method comprising: (a) statistically associating (i) one or more genetic variants in a population of neovascular age-related macular degeneration subjects who have been administered an intravitreal anti-VEGF agent with (ii) an anatomical outcome in the same population of neovascular age-related macular degeneration subjects, wherein one or more genetic variants is associated with the presence of intraretinal cystoid edema (fluid), compared to the absence of intraretinal cystoid edema (fluid) after one year of treatment.

Examples of anti-VEGF agent or intravitreal anti-VEGF agent include, but is not limited to, bevacizumab, ranibizumab, ramucirumab, aflibercept, sunitinib, sorafenib, vandetanib, vatalanib, tivozanib, axitinib, imatinib or pazopanib Disclosed herein are methods of associating a genetic variant with visual acuity, anatomic outcomes or treatment frequency, the method comprising: comparing the anatomical outcome in the population of neovascular age-related macular degeneration subjects who have been administered an intravitreal anti-VEGF agent and who have one or two copies of the genetic variant allele with the anatomical outcome of a population of neovascular age-related macular degeneration subjects who have been administered an intravitreal anti-VEGF agent and who do not have a copy of the genetic variant allele; and statistically associating (i) one or more genetic variants in a population of neovascular age-related macular degeneration subjects who have been administered an intravitreal anti-VEGF agent with (ii) an anatomical outcome in the same population of neovascular age-related macular degeneration subjects.

Disclosed herein are methods of associating a genetic variant with visual acuity, anatomic outcomes or treatment frequency, the method comprising: (a) statistically associating (i) one or more genetic variants in a population of neovascular age-related macular degeneration subjects who have been administered an intravitreal anti-VEGF agent for one year with (ii) an anatomical outcome in the same population of neovascular age-related macular degeneration subjects, wherein one or more genetic variants is associated with the presence of intraretinal cystoid edema (fluid) in subjects who have one or two copies of the genetic variant allele, compared to the level of intraretinal cystoid edema (fluid) in subjects who do not have a copy of the genetic variant allele.

Disclosed herein are methods of associating a genetic variant with visual acuity, anatomic outcomes or treatment frequency, the method comprising: comparing the anatomical outcome in the population of neovascular age-related macular degeneration subjects who have been administered an intravitreal anti-VEGF agent and who have one or two copies of the genetic variant allele with the anatomical outcome of a population of neovascular age-related macular degeneration subjects who have been administered an intravitreal anti-VEGF agent and who do not have a copy of the genetic variant allele; and statistically associating (i) one or more genetic variants in a population of neovascular age-related macular degeneration subjects who have been administered an intravitreal anti-VEGF agent with (ii) an anatomical outcome in the same population of neovascular age-related macular degeneration subjects, wherein DNA samples from the subjects are genotyped prior to the step of statistical association. In some aspects, the anatomic outcome is a Gain of 15 letters (visual acuity). In some aspects, the treatment frequency can reflect an ongoing requirement for aggressive treatment with an intravitreal anti-VEGF agent after one full year of dosing.

The statistical associations described herein can include logistic regression analyses, QC of the genetic data including Hardy-Weinberg Equilibrium (HWE) tests, identity by state (IBS) estimates and/or gender confirmation. The population structure can be assessed using principal component analysis (PCA). The statistical associations can include logistic regression with baseline values and any potential population structure variables as covariates in the model.

In some aspects the anatomical outcome is the presence of intraretinal cystoid edema, a gain in vision/improved visual acuity, or a decrease in intraretinal fluid. Additional anatomical outcomes that can be used include, but are not limited to, a reduction in central retinal thickness as measured by optical coherence tomography (OCT), complete resolution of both intraretinal and subretinal fluid, reduction in choroidal neovascular (CNV) area, reduction in total neovascular lesion size as measured by fluorescence angiography, and reduction in subretinal hyperreflectivity (SHM) material as measured by OCT.

In some aspects, the statistical association can be measured as a p-value. For example different types of p-values can be obtained: simple t-test p-values for the original data and log-transformed data both assuming equal variances, and chebby checker p-values. These p-values can be presented on an individual basis as well as by taking multiple comparisons into account. The mix-o-matic method can be applied to provide additional information about these p-values. In some aspects, the p-value of the association is less than or equal to $1\times10^{-5}$, $1\times10^{-6}$, $1\times10^{-7}$, $1\times10^{-8}$, etc. In some aspects, the p-value of the association is less than or equal to $1\times10^{-5}$, i.e., suggestive statistical significant and $1\times10^{-8}$ i.e. experiment wise statistical significance.

In some aspects, the effect size of a statistical association can be measured as an odds ratio. For example, the effect size of a statistical association can be measured as the ratio of the odds of the presence of intraretinal cystoid edema (fluid) in neovascular age-related macular degeneration subjects treated with an intravitreal anti-VEGF agent and who have 1 or 2 copies of an allele, to the ratio of the odds of the presence of intraretinal cystoid edema (fluid) in neovascular age-related macular degeneration subjects treated with an intravitreal anti-VEGF agent and who do not have the copy of the allele. In some aspects, the odds ratio is less than or equal to 0.2, 0.3, 0.4, 0.5, 0.6, 0.7, 0.8 or 0.9. Having one copy of the allele would have a smaller influence than individuals who have two copies of the allele.

In some aspects, the statistical association can be measured as the ratio of the odds of the Gain of 15 letters (visual acuity) in neovascular age-related macular degeneration subjects treated with an intravitreal anti-VEGF agent and who have 1 or 2 copies of an allele, to the ratio of the odds of the Gain of 15 letters in neovascular age-related macular degeneration subjects treated with an intravitreal anti-VEGF agent and who do not have the copy of the allele. In some aspects, the odds ratio is greater than or equal to 2.4, 2.5, 2.6, 2.7, 2.8 or 2.9.

In some aspects, the statistical association can be measured as the ratio of the odds of neovascular age-related macular degeneration subjects who have a higher requirement for on-going aggressive treatment with an intravitreal anti-VEGF agent and who have 1 or 2 copies of an allele, to the odds of neovascular age-related macular degeneration subjects who have a lower requirement for on-going aggressive treatment with an intravitreal anti-VEGF agent and who do not have the copy of the allele. In some aspects, the odds ratio is less than or equal to 4.0, 3.9, 3.8, 3.7, 3.6, 3.5, 3.4, 3.3, or 3.2

In some aspects the methods can be used to associate a genetic variant with visual acuity, anatomic outcomes or treatment frequency. In some aspects, the genetic variant can be one or more single nucleotide polymorphisms.

Disclosed herein are methods of associating a genetic variant with visual acuity, anatomic outcomes or treatment frequency, the method comprising: (a) statistically associating (i) one or more genetic variants in a population of neovascular age-related macular degeneration subjects who have been administered an intravitreal anti-VEGF agent with (ii) an anatomical outcome in the same population of neovascular age-related macular degeneration subjects, wherein one or more genetic variants is associated with a reduced level of presence of intraretinal cystoid edema (fluid), after one year of treatment.

Disclosed herein are methods of associating a genetic variant with visual acuity, anatomic outcomes or treatment frequency, the method comprising: (a) statistically associating (i) one or more genetic variants in a population of neovascular age-related macular degeneration subjects who have been administered an intravitreal anti-VEGF agent with (ii) an anatomical outcome in the same population of neovascular age-related macular degeneration subjects, wherein the one or more genetic variants is associated with a decreased level of intraretinal fluid in subjects who have 1 or 2 copies of a genetic variant allele, compared to the level of intraretinal fluid in neovascular age-related macular degeneration subjects administered an intravitreal anti-VEGF agent and who do not have a copy of the genetic variant allele.

Disclosed herein are methods of associating a genetic variant with visual acuity, anatomic outcomes or treatment frequency, the method comprising: (a) statistically associating (i) one or more genetic variants in a population of neovascular age-related macular degeneration subjects who have been administered an intravitreal anti-VEGF agent with (ii) an anatomical outcome in the same population of neovascular age-related macular degeneration subjects, wherein one or more genetic variants is associated with a the presence of intraretinal cystoid edema (fluid), compared to the absence of intraretinal cyctoid edema (fluid) after one year of treatment.

Disclosed herein are methods of associating a genetic variant with visual acuity, anatomic outcomes or treatment frequency, the method comprising: (a) statistically associating (i) one or more genetic variants in a population of neovascular age-related macular degeneration subjects who have been administered an intravitreal anti-VEGF agent with (ii) an anatomical outcome in the same population of neovascular age-related macular degeneration subjects, wherein the one or more genetic variants is associated with a decreased intraretinal fluid, compared to the level of intraretinal fluid in neovascular age-related macular degeneration subjects not treated with an intravitreal anti-VEGF agent, wherein the genetic variant is a single nucleotide polymorphism is selected from the group consisting of rs2056688, rs5962084, rs5962087, rs5915722 and rs5962095. In some aspects, the genetic variant is a single nucleotide polymorphism selected from the group consisting of rs2056688, rs5962084, rs5962087, rs5915722, rs5962095, rs2106124, rs1879796, rs12148845, rs12148100, rs17482885 and rs17629019.

Disclosed herein are methods of associating a genetic variant with visual acuity, anatomic outcomes or treatment frequency, the method comprising: (a) statistically associating (i) one or more genetic variants in a population of neovascular age-related macular degeneration subjects who have been administered an intravitreal anti-VEGF agent with (ii) an anatomical outcome in the same population of neovascular age-related macular degeneration subjects, wherein one or more genetic variants is associated with a the presence of intraretinal cystoid edema (fluid), compared to the absence of intraretinal cystoid edema (fluid) after one year of treatment.

Disclosed herein are methods of associating a genetic variant with intraretinal fluid, the method comprising: statistically associating (a) one or more genetic variants in a population of neovascular age-related macular degeneration subjects with (b) intraretinal fluid in the same population of neovascular age-related macular degeneration subjects, wherein the one or more genetic variants is associated with reduced intraretinal fluid in neovascular age-related macular degeneration subjects treated with an intravitreal anti-VEGF agent, compared to the level of intraretinal fluid in neovascular age-related macular degeneration subjects not treated with an intravitreal anti-VEGF agent, wherein reduced intraretinal fluid is improved visual acuity in in neovascular age-related macular degeneration subjects treated with an intravitreal anti-VEGF agent, compared to the level of intraretinal fluid in neovascular age-related macular degeneration subjects not treated with an intravitreal anti-VEGF agent.

Disclosed herein are methods of associating a genetic variant with visual acuity, anatomic outcomes or treatment frequency, the method comprising: (a) statistically associating (i) one or more genetic variants in a population of neovascular age-related macular degeneration subjects who have been administered an intravitreal anti-VEGF agent with (ii) an anatomical outcome in the same population of neovascular age-related macular degeneration subjects, wherein one or more genetic variants is associated with a the presence of intraretinal cystoid edema (fluid), compared to the absence of intraretinal cystoid edema (fluid) after one year of treatment.

Disclosed herein are methods of associating a genetic variant with intraretinal fluid, the method comprising: statistically associating (a) one or more genetic variants in a population of neovascular age-related macular degeneration subjects with (b) intraretinal fluid in the same population of neovascular age-related macular degeneration subjects, wherein the one or more genetic variants is associated with reduced intraretinal fluid in neovascular age-related macular degeneration subjects treated with an intravitreal anti-VEGF agent, compared to the level of intraretinal fluid in neovascular age-related macular degeneration subjects not treated with an intravitreal anti-VEGF agent, wherein the p-value of the association is less than or equal to $1 \times 10^{-6}$.

Disclosed herein are methods of associating a genetic variant with visual acuity, anatomic outcomes or treatment frequency, the method comprising: (a) statistically associating (i) one or more genetic variants in a population of neovascular age-related macular degeneration subjects who have been administered an intravitreal anti-VEGF agent with (ii) an anatomical outcome in the same population of neovascular age-related macular degeneration subjects, wherein one or more genetic variants is associated with a the presence of intraretinal cystoid edema (fluid), compared to the absence of intraretinal cystoid edema (fluid) after one year of treatment.

Disclosed herein are methods of associating a genetic variant with intraretinal fluid, the method comprising: statistically associating (a) one or more genetic variants in a population of neovascular age-related macular degeneration subjects with (b) intraretinal fluid in the same population of neovascular age-related macular degeneration subjects, wherein the one or more genetic variants is associated with reduced intraretinal fluid in neovascular age-related macular degeneration subjects treated with an intravitreal anti-VEGF agent, compared to the level of intraretinal fluid in neovascular age-related macular degeneration subjects not treated with an intravitreal anti-VEGF agent, wherein the odds ratio of reduced intraretinal fluid in neovascular age-related macular degeneration subjects treated with an intravitreal anti-VEGF agent to reduced intraretinal fluid in neovascular age-related macular degeneration subjects not treated with an intravitreal anti-VEGF agent is less than or equal to 0.5.

Disclosed herein are methods of associating a genetic variant with visual acuity, anatomic outcomes or treatment frequency, the method comprising: (a) statistically associating (i) one or more genetic variants in a population of neovascular age-related macular degeneration subjects who have been administered an intravitreal anti-VEGF agent with (ii) an anatomical outcome in the same population of neovascular age-related macular degeneration subjects, wherein one or more genetic variants is associated with a the presence of intraretinal cystoid edema (fluid), compared to the absence of intraretinal cystoid edema (fluid) after one year of treatment.

Disclosed herein are methods of associating a genetic variant with intraretinal fluid, the method comprising: statistically associating (a) one or more genetic variants in a population of neovascular age-related macular degeneration subjects with (b) intraretinal fluid in the same population of neovascular age-related macular degeneration subjects, wherein the one or more genetic variants is associated with reduced intraretinal fluid in neovascular age-related macular degeneration subjects treated with an intravitreal anti-VEGF agent, compared to the level of intraretinal fluid in neovascular age-related macular degeneration subjects not treated with an intravitreal anti-VEGF agent, wherein the genetic variant is a single nucleotide polymorphism.

Disclosed herein are methods of associating a genetic variant with visual acuity, anatomic outcomes or treatment frequency, the method comprising: (a) statistically associating (i) one or more genetic variants in a population of neovascular age-related macular degeneration subjects who have been administered an intravitreal anti-VEGF agent with (ii) an anatomical outcome in the same population of neovascular age-related macular degeneration subjects, wherein one or more genetic variants is associated with a the presence of intraretinal cystoid edema (fluid), compared to the absence of intraretinal cystoid edema (fluid) after one year of treatment.

Disclosed herein are methods of associating a genetic variant with intraretinal fluid, the method comprising: statistically associating (a) one or more genetic variants in a population of neovascular age-related macular degeneration subjects with (b) intraretinal fluid in the same population of neovascular age-related macular degeneration subjects, wherein the one or more genetic variants is associated with reduced intraretinal fluid in neovascular age-related macular degeneration subjects treated with an intravitreal anti-VEGF agent, compared to the level of intraretinal fluid in neovascular age-related macular degeneration subjects not treated with an intravitreal anti-VEGF agent, wherein the genetic variant is a single nucleotide polymorphism, wherein the single nucleotide polymorphism is selected from the group consisting of rs2056688, rs5962084, rs5962087, rs5915722 and rs5962095.

The present disclosure also provides methods of treating a subject having macular degeneration. In some embodiments, the treatment methods comprise a genotyping component based on the genotypes, genetic variants, SNPs, and/or association methods described or exemplified herein, carried out on a subject before the subject has been treated with a vascular endothelial growth factor (VEGF) inhibitor. In some embodiments, the treatment methods comprise a genotyping component based on the genotypes, genetic variants, SNPs, and/or association methods described or exemplified herein, carried out on a subject after the subject has been treated with a VEGF inhibitor for at least about one year, or has been treated with a VEGF inhibitor for a number (e.g., 2, 3, 5, 7, 9, etc.) of months within the first year of a treatment regimen. In such embodiments, the genotyping can, for example, set expectations concerning the potential outcomes from an initial (e.g., first year) dosing regimen with a VEGF inhibitor. By way of example, the subject may have one or more gene variants associated with improved visual acuity and/or anatomic outcomes from treatment with a VEGF inhibitor such as aflibercept, such that identification of such variants (or lack thereof) in the subject informs of how visual acuity and/or anatomic outcome are likely to change after the first year of treatment with the VEGF inhibitor. Then, following the first year of treatment with the VEGF inhibitor, the subject's genotype may be used as part of a reassessment protocol to make modifications to the VEGF inhibitor treatment regimen, especially with respect to the dosing frequency (e.g., how frequently the VEGF inhibitor is administered).

This reassessment at the end of the about one year treatment (or initially prior to the beginning of any treatment regimen) may be accompanied by a physician's evaluation of the subject's eye (e.g., retina). In some embodiments, a subject is evaluated about every 3 to 5 weeks after the first year of treatment. In some embodiments, a subject is evaluated about every 4 weeks after the first year of treatment. The evaluation can include determining whether any one or more of the following has or is occurring in the subjects eye: i) increase in central retinal thickness of ≥100 μm compared to the lowest previous value as measured by Optical Coherence Tomography (OCT); ii) a loss from the best previous letter score of 5 ETDRS letters in conjunction with recurrent fluid as indicated by OCT; iii) new or persistent fluid as indicated by OCT; iv) new onset of classic neovascularization; v) new or persistent leak on Fluorescein Angiography (FA); vi) new macular hemorrhage; and/or vii) 12 weeks have elapsed since the previous injection. Upon occurrence of any one or more of these features, the subject's injection regimen after the first year of initial treatment (or at the beginning of the initial treatment) may be increased in frequency as described herein.

Based, in part, on the subject's genotype and on the subject's response (e.g., changes (positive, negative, or none) in visual acuity and/or one or more anatomic outcomes) after about a year of a treatment regimen based on administration of a VEGF inhibitor, the dosing frequency of the treatment regimen may be modified. For example, the dosing frequency may be shortened or elongated. The modifications to the dosing frequency may follow a clinician's evaluation of the subject's visual acuity and/or one or more anatomic outcomes as part of a reassessment process following the initial treatment protocol (e.g., first year of VEGF inhibitor administration) has been carried out on the subject.

By way of example, during the first year of treatment, a subject may receive a treatment regimen comprising administering about 2 mg of a VEGF inhibitor such as aflibercept (e.g., EYLEA®) about every 4 weeks for a period of about 3 months, followed by administering about 2 mg of the VEGF inhibitor about every 8 weeks for a period of about 9 months. When the subject does not have one or more gene variants associated with improved visual acuity and/or anatomic outcomes from treatment with a VEGF inhibitor, and when the patient does not exhibit improved visual acuity and/or an improvement in one or more anatomic outcomes after about one year of administering the VEGF inhibitor, the dosing frequency may be reduced from administration every 8 weeks to about every 7 weeks, to about every 6 weeks, to about every 5 weeks, or to about every 4 weeks. Further periodic reassessments by the clinician may be used to further reduce, or increase, as the case may be, the dosing frequency in order to bring about improvement in visual acuity and/or one or more anatomic outcomes from treatment with a VEGF inhibitor. For example, as a result of one or more further periodic reassessments, the dosing frequency may be further reduced from about every 6 weeks to about every 4 weeks, or about every 7 weeks to about every 6 weeks, etc.

When the subject has one or more gene variants associated with improved visual acuity and/or anatomic outcomes from treatment with a VEGF inhibitor, and when the subject exhibits improved visual acuity and/or an improvement in one or more anatomic outcomes after one year of administering the VEGF inhibitor, the dosing frequency may be increased from every 8 weeks to administration about every 9 weeks, to about every 10 weeks, to about every 11 weeks, to about every 12 weeks, to about every 13 weeks, to about every 14 weeks, to about every 15 weeks, or to about every 16 weeks. One or more further periodic reassessments by the clinician may be used to further increase, or reduce, as the case may be, the dosing frequency in order to sustain or bring about further improvement in visual acuity and/or one or more anatomic outcomes from treatment with a VEGF inhibitor, as well as compliance with the treatment regimen. For example, as a result of one or more further periodic reassessments, the dosing frequency may be further increased from about every 10 weeks to about every 12 weeks, or about every 9 weeks to about every 10 weeks, etc.

Thus, the methods of treatment may comprise the steps of: a) determining whether the subject has one or more genetic variants associated with visual acuity and/or anatomic outcome by performing or having performed a genotype assay on a DNA sample obtained from the subject to determine if the subject has one or more genetic variants associated with improved visual acuity and/or anatomic outcome, and i) when the subject has one or more of the genetic variants associated with improved visual acuity and/or anatomic outcome, and when the subject exhibits improved visual acuity and/or improvements in one or more anatomic outcomes after about one year of administering the VEGF inhibitor to the subject, increasing the dosing frequency of administering the VEGF inhibitor to the subject from about every 8 weeks to about every 9 to 16 weeks, to about every 9 to 15 weeks, to about every 9 to 14 weeks, to about every 9 to 13 weeks, to about every 9 to 12 weeks, to about every 9 to 11 weeks, to about every 9 to 10 weeks, to about every 10 to 16 weeks, to about every 10 to 15 weeks, to about every 10 to 14 weeks, to about every 10 to 13 weeks, to about every 10 to 12 weeks, to about every 10 to 11 weeks, to about every 11 to 16 weeks, to about every 11 to 15 weeks, to about every 11 to 14 weeks, to about every 11 to 13 weeks, to about every 11 to 12 weeks, to about every 12 to 16 weeks, to about every 12 to 15 weeks, to about every 12 to 14 weeks, to about every 12 to 13 weeks, to about every 13 to 16 weeks, to about every 13 to 15 weeks, to about every 13 to 14 weeks, to about every 14 to 16 weeks, to about every 14 to 15 weeks, or to about every 15 to 16 weeks. In some embodiments, the dosing frequency of administering the VEGF inhibitor to the subject is increased from about every 8 weeks to about every 9 to 12 weeks.

In some embodiments, the methods of treatment may comprise the steps of: a) determining whether the subject has one or more genetic variants associated with visual acuity and/or anatomic outcome by performing or having performed a genotype assay on a DNA sample obtained from the subject to determine if the subject has one or more genetic variants associated with improved visual acuity and/or anatomic outcome, and i) when the subject has one or more of the genetic variants associated with improved visual acuity and/or anatomic outcome, and when the subject exhibits improved visual acuity and/or improvements in one or more anatomic outcomes after about one year of administering the VEGF inhibitor to the subject, increasing the dosing frequency of administering the VEGF inhibitor to the subject from about every 8 weeks to about every 16 weeks. In some alternative embodiments, the method comprises i) when the subject has one or more of the genetic variants associated with improved visual acuity and/or anatomic outcome, and when the subject exhibits improved visual acuity and/or improvements in one or more anatomic outcomes after about one year of administering the VEGF inhibitor to the subject, increasing the dosing frequency of administering the VEGF inhibitor to the subject from about every 8 weeks to about every 15 weeks. In some alternative embodiments, the method comprises i) when the subject has one or more of the genetic variants associated with improved visual acuity and/or anatomic outcome, and when the subject exhibits improved visual acuity and/or improvements in one or more anatomic outcomes after about one year of administering the VEGF inhibitor to the subject, increasing the dosing frequency of administering the VEGF inhibitor to the subject from about every 8 weeks to about every 14 weeks. In some alternative embodiments, the method comprises i) when the subject has one or more of the genetic variants associated with improved visual acuity and/or anatomic outcome, and when the subject exhibits improved visual acuity and/or improvements in one or more anatomic outcomes after about one year of administering the VEGF inhibitor to the subject, increasing the dosing frequency of administering the VEGF inhibitor to the subject from about every 8 weeks to about every 13 weeks. In some alternative embodiments, the method comprises i) when the subject has one or more of the genetic variants associated with improved visual acuity and/or anatomic outcome, and when the subject exhibits improved visual acuity and/or improvements in one or more anatomic outcomes after about one year of administering the VEGF inhibitor to the subject, increasing the dosing frequency of administering the VEGF inhibitor to the subject from about every 8 weeks to about every 12 weeks. In some alternative embodiments, the method comprises i) when the subject has one or more of the genetic variants associated with improved visual acuity and/or anatomic outcome, and when the subject exhibits improved visual acuity and/or improvements in one or more anatomic outcomes after about one year of administering the VEGF inhibitor to the subject, increasing the dosing frequency of administering the VEGF inhibitor to the subject from about every 8 weeks to about every 11 weeks. In some alternative embodiments, the method comprises i) when the subject has one or more of the genetic variants associated with improved visual acuity and/or anatomic outcome, and when the subject exhibits improved visual acuity and/or improvements in one or more anatomic outcomes after about one year of administering the VEGF inhibitor to the subject, increasing the dosing frequency of administering the VEGF inhibitor to the subject from about every 8 weeks to about every 10 weeks. In some alternative embodiments, the method comprises i) when the subject has one or more of the genetic variants associated with improved visual acuity and/or anatomic outcome, and when the subject exhibits improved visual acuity and/or improvements in one or more anatomic outcomes after about one year of administering the VEGF inhibitor to the subject, increasing the dosing frequency of administering the VEGF inhibitor to the subject from about every 8 weeks to about every 9 weeks.

In some alternative embodiments, the method comprises i) when the subject has one or more of the genetic variants associated with improved visual acuity and/or anatomic outcome, and when the subject exhibits improved visual acuity and/or improvements in one or more anatomic outcomes after about one year of administering the VEGF inhibitor to the subject, increasing the dosing frequency of administering the VEGF inhibitor to the subject to about every 9 weeks. In some alternative embodiments, the method comprises i) when the subject has one or more of the genetic variants associated with improved visual acuity and/or anatomic outcome, and when the subject exhibits improved visual acuity and/or improvements in one or more anatomic outcomes after about one year of administering the VEGF inhibitor to the subject, increasing the dosing frequency of administering the VEGF inhibitor to the subject to about every 10 weeks. In some alternative embodiments, the method comprises i) when the subject has one or more of the genetic variants associated with improved visual acuity and/or anatomic outcome, and when the subject exhibits improved visual acuity and/or improvements in one or more anatomic outcomes after about one year of administering the VEGF inhibitor to the subject, increasing the dosing frequency of administering the VEGF inhibitor to the subject to about every 11 weeks. In some alternative embodiments, the method comprises i) when the subject has one or more of the genetic variants associated with improved visual acuity and/or anatomic outcome, and when the subject exhibits improved visual acuity and/or improvements in one or more anatomic outcomes after about one year of administering the VEGF inhibitor to the subject, increasing the dosing frequency of administering the VEGF inhibitor to the subject to about every 12 weeks. In some alternative embodiments, the method comprises i) when the subject has one or more of the genetic variants associated with improved visual acuity and/or anatomic outcome, and when the subject exhibits improved visual acuity and/or improvements in one or more anatomic outcomes after about one year of administering the VEGF inhibitor to the subject, increasing the dosing frequency of administering the VEGF inhibitor to the subject to about every 13 weeks. In some alternative embodiments, the method comprises i) when the subject has one or more of the genetic variants associated with improved visual acuity and/or anatomic outcome, and when the subject exhibits improved visual acuity and/or improvements in one or more anatomic outcomes after about one year of administering the VEGF inhibitor to the subject, increasing the dosing frequency of administering the VEGF inhibitor to the subject to about every 14 weeks. In some alternative embodiments, the method comprises i) when the subject has one or more of the genetic variants associated with improved visual acuity and/or anatomic outcome, and when the subject exhibits improved visual acuity and/or improvements in one or more anatomic outcomes after about one year of administering the VEGF inhibitor to the subject, increasing the dosing frequency of administering the VEGF inhibitor to the subject to about every 15 weeks. In some alternative embodiments, the method comprises i) when the subject has one or more of the genetic variants associated with improved visual acuity and/or anatomic outcome, and when the subject exhibits improved visual acuity and/or improvements in one or more anatomic outcomes after about one year of administering the VEGF inhibitor to the subject, increasing the dosing frequency of administering the VEGF inhibitor to the subject to about every 16 weeks.

The methods of treatment may further comprise ii) when the subject does not have one or more of the genetic variants associated with improved visual acuity and/or anatomic outcome, and when the subject does not exhibit improved visual acuity and/or improvements in one or more anatomic outcomes after about one year of administering the VEGF inhibitor to the subject, decreasing the dosing frequency of administering the VEGF inhibitor to the subject from about every 8 weeks to about every 4 to 7 weeks, to about every 4 to 6 weeks, to about every 4 to 5 weeks, to about every 5 to 7 weeks, to about every 5 to 6 weeks, or to about every 6 to 7 weeks. In some embodiments, the dosing frequency of administering the VEGF inhibitor to the subject is decreased from about every 8 weeks to about every 4 to 6 weeks.

The methods of treatment may further comprise ii) when the subject does not have one or more of the genetic variants associated with improved visual acuity and/or anatomic outcome, and when the subject does not exhibit improved visual acuity and/or improvements in one or more anatomic outcomes after about one year of administering the VEGF inhibitor to the subject, decreasing the dosing frequency of administering the VEGF inhibitor to the subject from about every 8 weeks to about every 7 weeks. In some alternative embodiments, the method comprises ii) when the subject does not have one or more of the genetic variants associated with improved visual acuity and/or anatomic outcome, and when the subject does not exhibit improved visual acuity and/or improvements in one or more anatomic outcomes after about one year of administering the VEGF inhibitor to the subject, decreasing the dosing frequency of administering the VEGF inhibitor to the subject from about every 8 weeks to about every 6 weeks. In some alternative embodiments, the method comprises ii) when the subject does not have one or more of the genetic variants associated with improved visual acuity and/or anatomic outcome, and when the subject does not exhibit improved visual acuity and/or improvements in one or more anatomic outcomes after about one year of administering the VEGF inhibitor to the subject, decreasing the dosing frequency of administering the VEGF inhibitor to the subject from about every 8 weeks to about every 5 weeks. In some alternative embodiments, the method comprises ii) when the subject does not have one or more of the genetic variants associated with improved visual acuity and/or anatomic outcome, and when the subject does not exhibit improved visual acuity and/or improvements in one or more anatomic outcomes after about one year of administering the VEGF inhibitor to the subject, decreasing the dosing frequency of administering the VEGF inhibitor to the subject from about every 8 weeks to about every 4 weeks.

In some alternative embodiments, the method comprises ii) when the subject does not have one or more of the genetic variants associated with improved visual acuity and/or anatomic outcome, and when the subject does not exhibit improved visual acuity and/or improvements in one or more anatomic outcomes after about one year of administering the VEGF inhibitor to the subject, decreasing the dosing frequency of administering the VEGF inhibitor to the subject to about every 7 weeks. In some alternative embodiments, the method comprises ii) when the subject does not have one or more of the genetic variants associated with improved visual acuity and/or anatomic outcome, and when the subject does not exhibit improved visual acuity and/or improvements in one or more anatomic outcomes after about one year of administering the VEGF inhibitor to the subject, decreasing the dosing frequency of administering the VEGF inhibitor to the subject to about every 6 weeks. In some alternative embodiments, the method comprises ii) when the subject does not have one or more of the genetic variants associated with improved visual acuity and/or anatomic outcome, and when the subject does not exhibit improved visual acuity and/or improvements in one or more anatomic outcomes after about one year of administering the VEGF inhibitor to the subject, decreasing the dosing frequency of administering the VEGF inhibitor to the subject to about every 5 weeks. In some alternative embodiments, the method comprises ii) when the subject does not have one or more of the genetic variants associated with improved visual acuity and/or anatomic outcome, and when the subject does not exhibit improved visual acuity and/or improvements in one or more anatomic outcomes after about one year of administering the VEGF inhibitor to the subject, decreasing the dosing frequency of administering the VEGF inhibitor to the subject to about every 4 weeks.

As part of the treatment methods, the one or more genetic variants associated with improved visual acuity and/or anatomic outcome may comprise a single nucleotide polymorphism (SNP). The SNP may comprise one or more of rs2056688, rs5962084, rs5962087, rs5915722, rs5962095, rs2106124, rs1879796, rs12148845, rs12148100, rs17482885, and rs17629019. In some preferred embodiments, the SNP comprises one or more of rs2056688, rs5962084, rs5962087, rs5915722, and rs5962095. In some preferred embodiments, the SNP is rs2056688.

As part of the treatment methods, the VEGF inhibitor is one or more of bevacizumab, ranibizumab, ramucirumab, aflibercept, sunitinib, sorafenib, vandetanib, vatalanib, tivozanib, axitinib, imatinib or pazopanib. In some preferred embodiments, the VEGF inhibitor is ranibizumab or aflibercept. In some preferred embodiments, the VEGF inhibitor is aflibercept.

As part of the treatment methods, an improved visual acuity may comprise a gain of letters. An improved visual acuity may comprise a gain of about 5 or more letters. An improved visual acuity may comprise a gain of about 10 or more letters. An improved visual acuity may comprise a gain of about 15 or more letters.

As part of the treatment methods, an improved anatomic outcome may comprise one or more of decreased intraretinal cystoid edema, a reduction in central retinal thickness, a complete resolution of both intraretinal and subretinal fluid, a reduction in choroidal neovascular (CNV) area, a reduction in total neovascular lesion size, or a reduction in subretinal hyperreflectivity (SHM) material. In some preferred embodiments, the improved anatomic outcome is decreased intraretinal fluid.

As part of the treatment methods, the VEGF inhibitor may be administered by intraocular injection. In some embodiments, the dose of the VEGF inhibitor is from about 1 to about 3 mg per injection. In some embodiments, the dose of the VEGF inhibitor is 2 mg per injection.

Kits

Also described herein are kits for utilizing the methods described herein. The kits described herein can comprise an assay or assays for detecting one or more genetic variants in a sample of a subject.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

VIEW 1 and VIEW 2 are Phase III clinical studies (VEGF Trap-Eye: Investigation of Efficacy and Safety in Wet AMD) of neovascular age-related macular degeneration (AMD), in which treatment subjects received intravitreal injection of aflibercept (Heier J S, et al., Am. Acad. Opthalmol. 119: 2537 (2012)).

The purpose of this statistical study was to identify genetic variants associated with anti-VEGF drug response as measured by visual acuity, anatomic outcomes and treatment frequency in the VIEW 1 study. An overview of the VIEW 1 Study is represented in FIG. 1. The VIEW 1 study evaluated efficacy and safety of intravitreal aflibercept injection (IAI) compared with ranibizumab for treatment of neovascular AMD.

At week 52, all IAI groups demonstrated similar improvements in all visual acuity endpoints compared to Rq4. Incidences of ocular adverse events were similar across all treatment groups; adverse events occurring in >10% of patients were conjunctival hemorrhage, eye pain, retinal hemorrhage, and reduced visual acuity.

Figure 3:
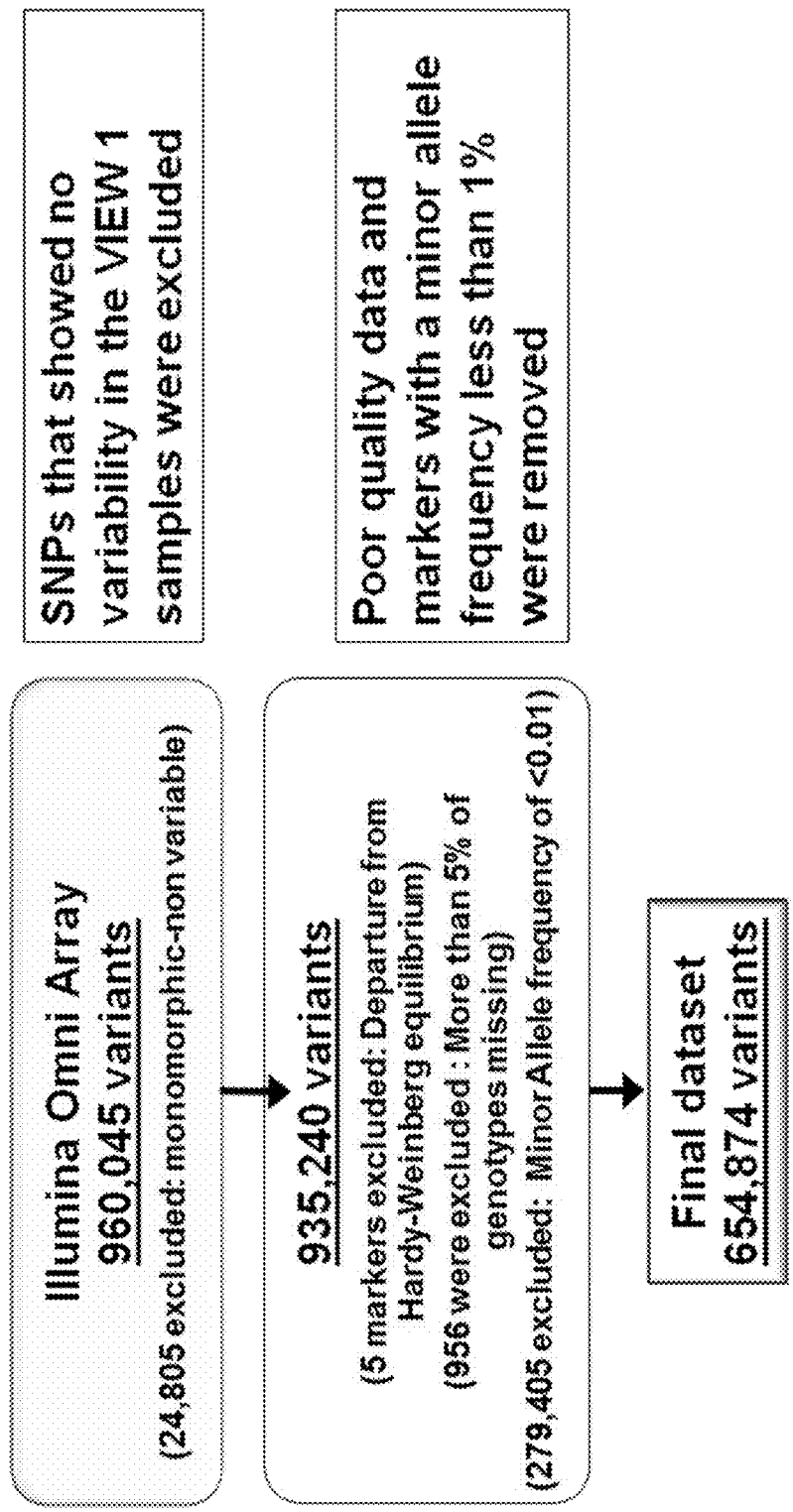
FIG. 3 shows quality control measures applied to SNPs on chip to generate a final sample set for the VIEW 1 study in 154 sites in the U.S. and Canada (~96% Caucasian randomized).
Figure 4:
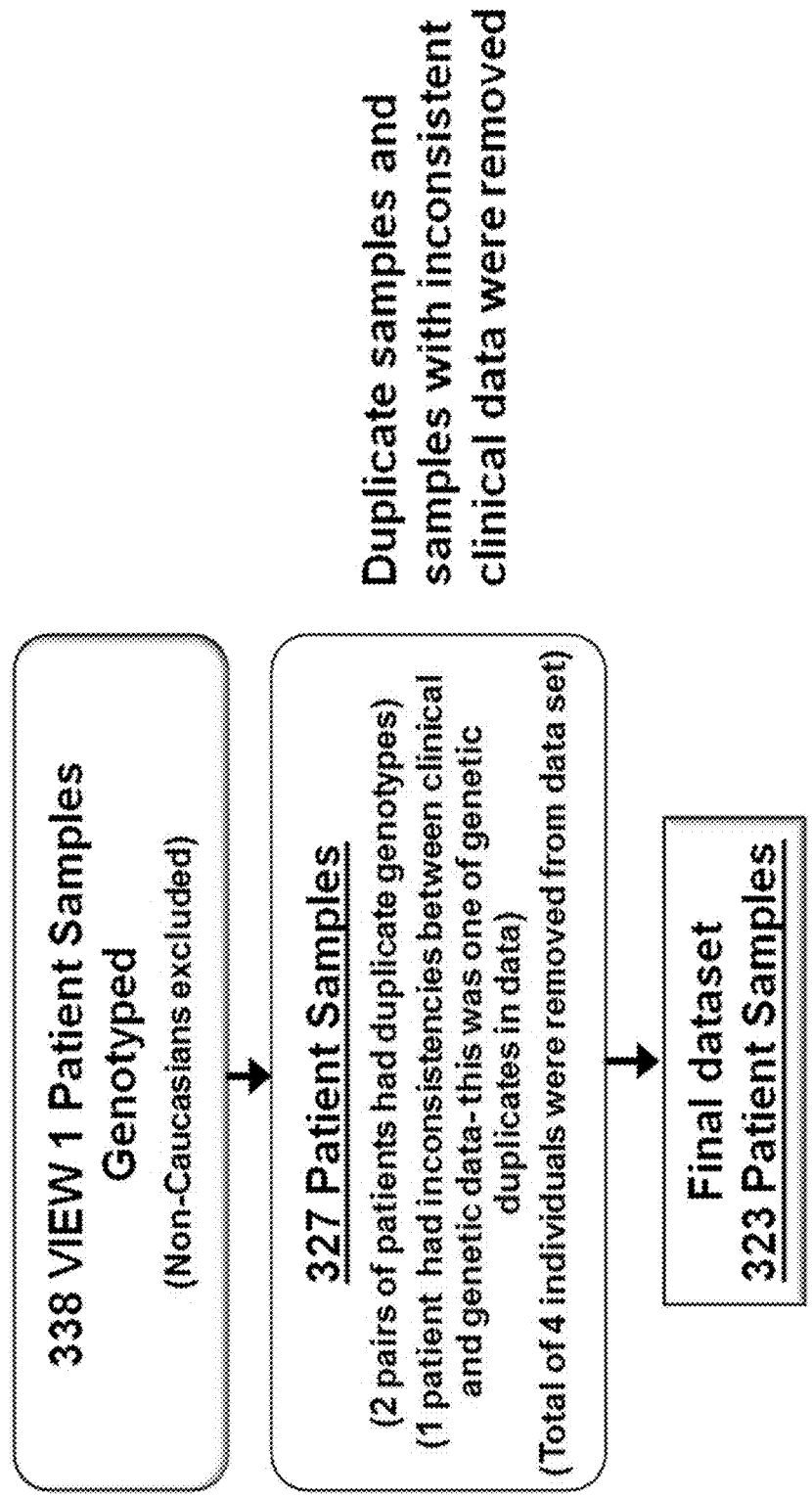
FIG. 4 shows quality control measures applied to SNPs on chip to generate a final sample set for the VIEW 1 study.

A genome wide association study (GWAS) was conducted on 362 VIEW 1 patients. DNA samples were genotyped using the Illumina Omni Express Exome Chip. Logistic regression with baseline values was performed to establish the association between genetic variants and efficacy variables. GWAS analysis of approximately 1 million variants was performed. The association between genetic variants and efficacy variables were determined using logistic regression with baseline values. All treatment arms were combined. For each SNP, genotypes were coded according to an additive mode of inheritance. Variants associated with gaining ETDRS letters at week 52, presence of intraretinal cystoid edema (fluid as measured by time domain optical coherence tomography (TD-OCT)) at week 52 and frequency of treatment at week 96 were evaluated. Variants were also associated with treatment burden. Specifically, patients requiring more than 7 injections from Week 52 to Week 96 [2nd Year of Study] were analyzed. In addition, variants were associated with the presence of intra-retinal cystoid edema (Defined as Fluid) at Week 52. Patient demographics and baseline characteristics of VIEW 1 were also identified. (See FIG. 2). Quality control measures were applied to SNPs on chip to generate a final sample set. (See FIGS. 3 and 4).

Figure 5:
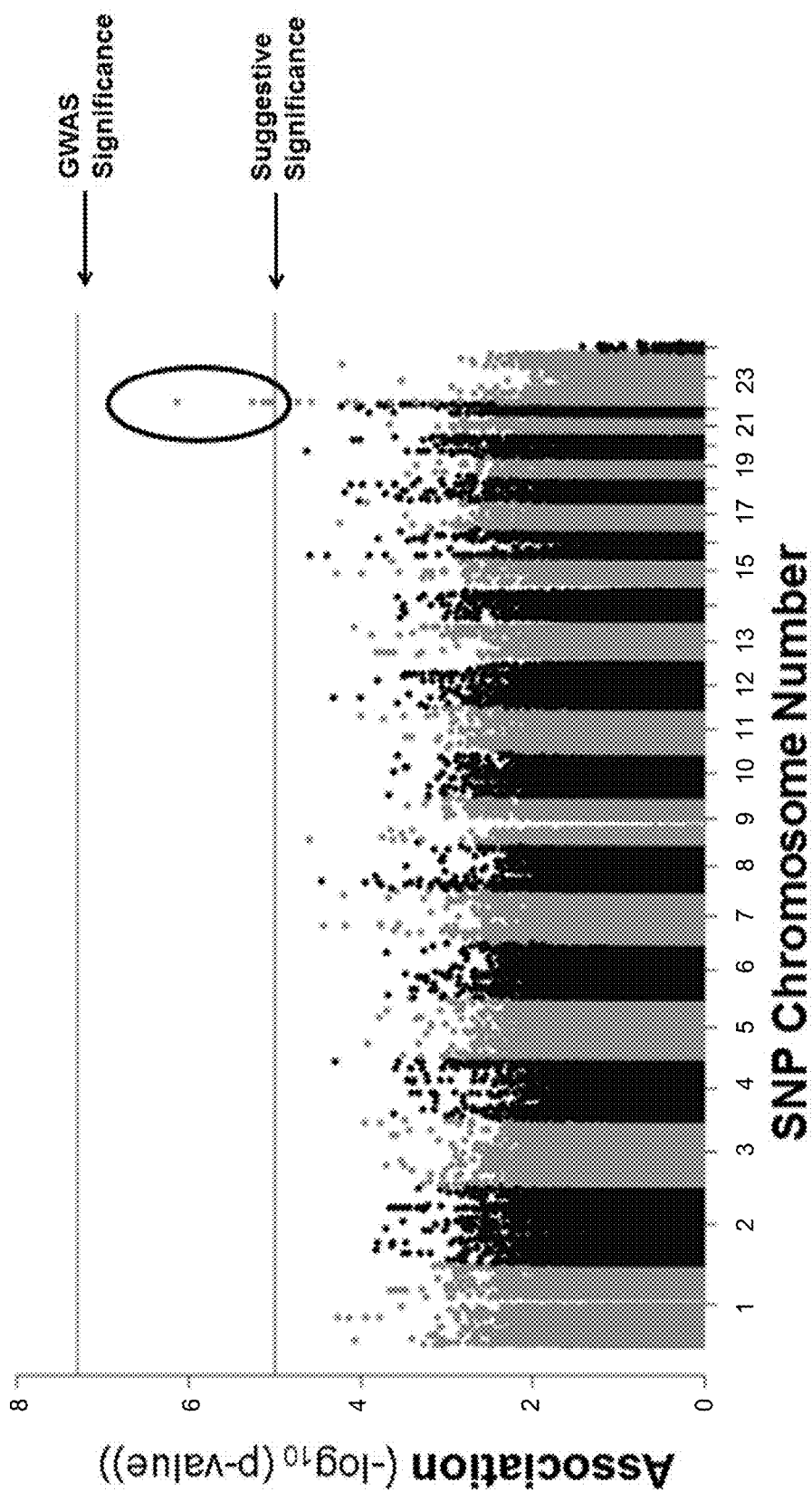
FIG. 5 shows an anatomical response, namely the X-chromosome SNP (r52056688), which revealed the highest association with anatomical outcome, demonstrating an odds ratio (OR) of 0.2578 and a point-wise association (p-value $7.27 \times 10^{-7}$) with presence of intraretinal fluid at week 52.

Anatomical response, namely the X-chromosome SNP (r52056688) revealed the highest association with anatomical outcome, demonstrating an odds ratio (OR) of 0.2578 and a point-wise association (p-value $7.27 \times 10^{-7}$) with presence of intraretinal fluid at week 52. (See FIG. 5).

Figure 6:
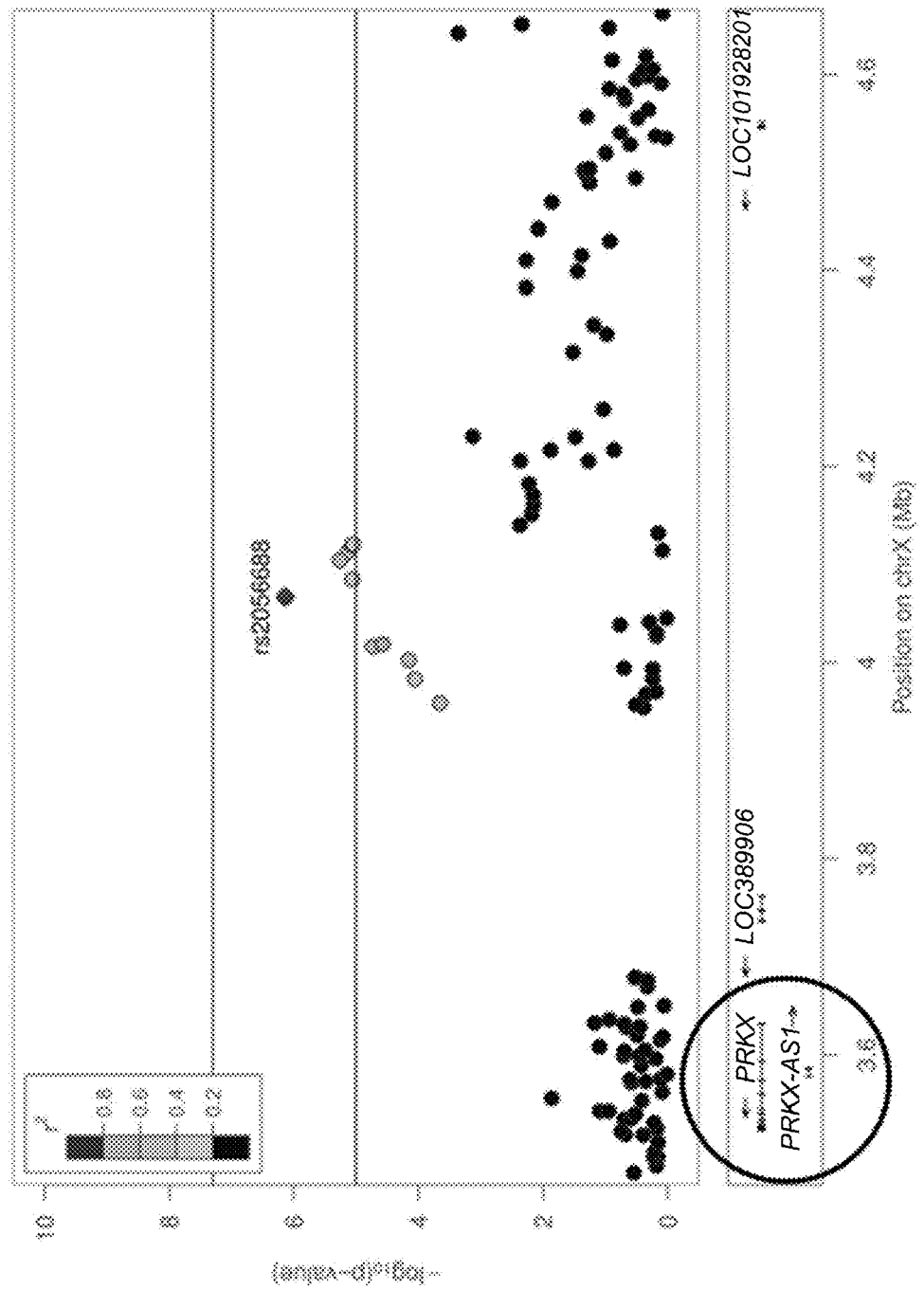
FIG. 6 shows the rs2056688 SNP was located in a non-coding region, with the closest relevant functional gene (Protein Kinase X-Linked (PRK-X)) mapping ~400 kb upstream of the putative variant.

Four neighboring SNPs (r55962084, rs5962087, rs5915722, r55962095) revealed similar ORs (0.3151-0.3461) and point-wise associations ($5.48 \times 10^{-6}$-$8.59 \times 10^{-6}$). The rs2056688 SNP was located in a non-coding region, with the closest relevant functional gene (Protein Kinase X-Linked (PRK-X)) mapping ~400 kb upstream of the putative variant. (See FIG. 6). Additional SNPs with lower significance were found in association with proportion of patients with ETDRS letters gains in vision at week 52 and frequency of treatment at week 96.

Figure 7:
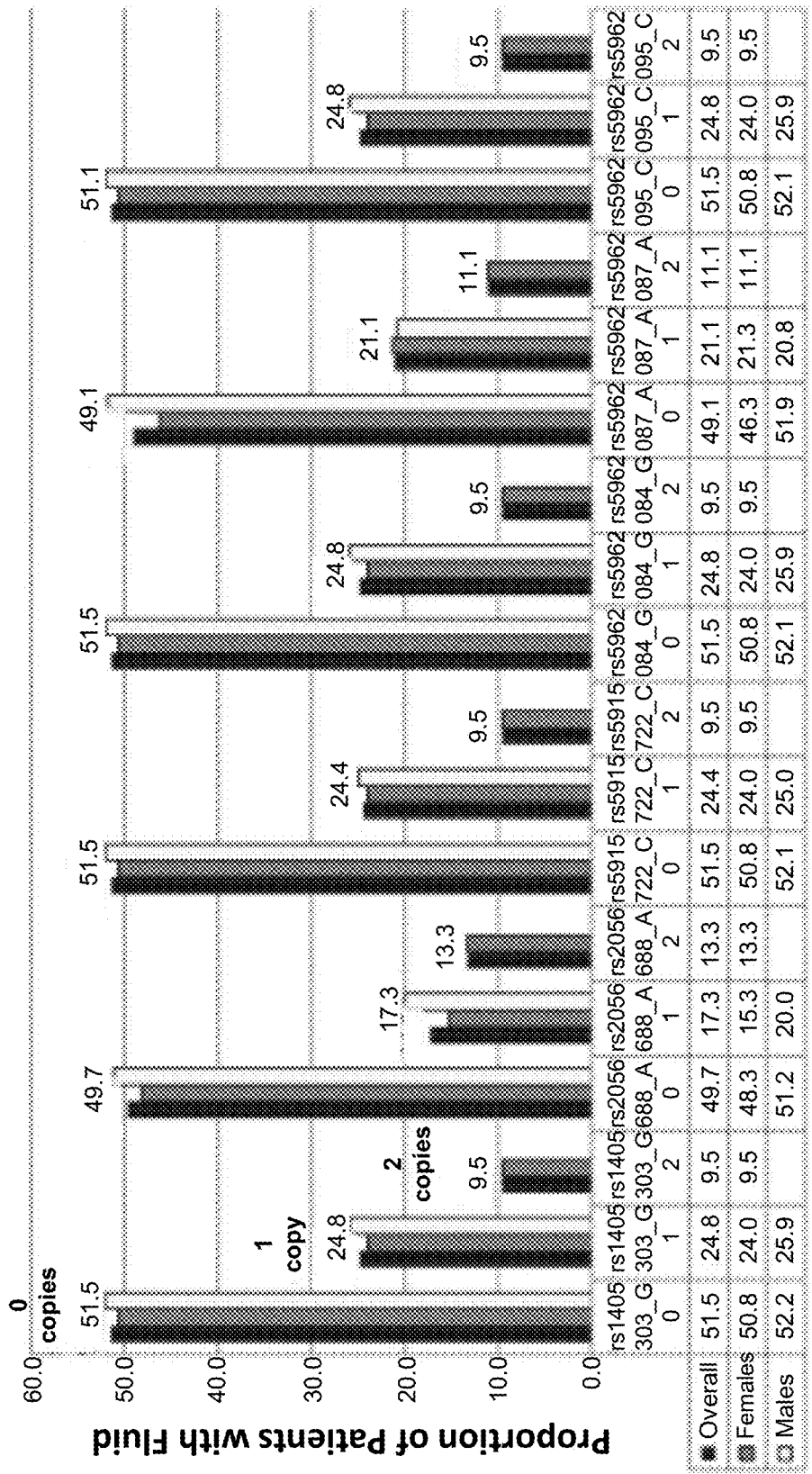
FIG. 7 shows additional neighboring SNPs showed a dose effect.

Additional neighboring SNPs showed a dose effect. Increasing the number of variant copies from 0→1→2 was found to reduce the likelihood of fluid present at Week 52 from ~50% to ~25% to ~10%. (See FIG. 7). FIG. 8 summarizes the SNPs identified in the study.

Conclusions: A GWAS in neovascular AMD patients undergoing anti-VEGF treatment in the VIEW 1 trial identified a suggestive association between a genetic variant and the presence of intraretinal fluid at week 52 as measured by TD-OCT. The variant was located at a position on the X chromosome near the gene for PRK-X, a serine/threonine protein kinase involved in angiogenesis.

What is claimed is:

1. A method for treating a macular degeneration patient with aflibercept, the method comprising:
    administering to the patient having one or more genetic variants of human vascular endothelial growth factor (VEGF) selected from the group consisting of rs2056688, rs5962084, rs5962087, rs5915722, and rs5962095 an initial treatment comprising intravitreal injection of about 2 mg of aflibercept about every 8 weeks;

evaluating the patient for intraretinal fluid following the initial treatment with aflibercept; and administering to the patient by intravitreal injection about 2 mg of aflibercept at a dosage frequency of about every 4 to 7 weeks if intraretinal fluid is present in the patient; or administering to the patient by intravitreal injection about 2 mg of aflibercept at a dosage frequency of about every 9 to 12 weeks if intraretinal fluid is not present in the patient.

2. The method of claim 1, wherein the initial treatment comprises intravitreal injection of about 2 mg of aflibercept about every 8 weeks for about 9 months.

3. The method of claim 1, wherein the dosing frequency if intraretinal fluid is present in the patient is about 4 to 6 weeks.

4. The method of claim 1, wherein the patient is evaluated for intraretinal fluid using time domain optical coherence tomography (TD-OCT).

5. A method for treating a macular degeneration patient with aflibercept, the method comprising:

evaluating the patient having one or more genetic variants of human vascular endothelial growth factor (VEGF) selected from the group consisting of rs2056688, rs5962084, rs5962087, rs5915722, and rs5962095 for intraretinal fluid; and administering to the patient by intravitreal injection about 2 mg of aflibercept at a dosing frequency of about every 4 to 7 weeks if intraretinal fluid is present in the patient; or administering to the patient by intravitreal injection about 2 mg of aflibercept at a dosing frequency of about every 9 to 16 weeks if intraretinal fluid is not present in the patient;

wherein, prior to evaluating the patient for intraretinal fluid, the patient received an initial treatment comprising intravitreal injection with aflibercept.

6. The method of claim 5, wherein, prior to evaluating the patient for intraretinal fluid, the patient received an initial treatment comprising intravitreal injection with aflibercept for at least about 3 months.

7. The method of claim 6, wherein the initial treatment comprises administering to the patient about 2 mg of aflibercept by intravitreal injection about every 8 weeks.

8. The method of claim 6, wherein, prior to evaluating the patient for intraretinal fluid, the patient received initial treatment comprising intravitreal injection with aflibercept for at least about one year.

9. The method of claim 5, wherein the dosing frequency if intraretinal fluid is present in the patient is about 4 to 6 weeks.

10. The method of claim 5, wherein the patient is evaluated for intraretinal fluid using time domain optical coherence tomography (TD-OCT).

11. A method for treating a macular degeneration patient with aflibercept, the method comprising:

evaluating the level of intraretinal fluid in the patient having one or more genetic variants of human vascular endothelial growth factor (VEGF) selected from the group consisting of rs2056688, rs5962084, rs5962087, rs5915722, and rs5962095 about every 3 to 5 weeks; and administering to the patient by intravitreal injection about 2 mg of aflibercept at a dosing frequency of about every 4 to 7 weeks if the level of intraretinal fluid in the patient has not decreased from the prior evaluation; or administering to the patient by intravitreal injection about 2 mg of aflibercept at a dosing frequency of about every 9 to 16 weeks if the level of intraretinal fluid in the patient has decreased from the prior evaluation;

wherein, prior to evaluating the level of intraretinal fluid in the patient, the patient received an initial treatment comprising intravitreal injection with aflibercept.

12. The method of claim 11, wherein, prior to evaluating the patient for intraretinal fluid, the patient received an initial treatment comprising intravitreal injection with aflibercept for at least about 3 months.

13. The method of claim 12, wherein the initial treatment comprises administering to the patient about 2 mg of aflibercept by intravitreal injection about every 8 weeks.

14. The method of claim 11, wherein, prior to evaluating the patient for intraretinal fluid, the patient received an initial treatment comprising intravitreal injection with aflibercept for at least about one year.

15. The method of claim 11, wherein the patient is evaluated for intraretinal fluid using time domain optical coherence tomography (TD-OCT).

16. A method for treating a macular degeneration patient with aflibercept, the method comprising:

evaluating whether the patient having one or more genetic variants of human vascular endothelial growth factor (VEGF) selected from the group consisting of rs2056688, rs5962084, rs5962087, rs5915722, and rs5962095 has an anatomic outcome selected from the group consisting of resolution of intraretinal fluid, resolution of subretinal fluid, reduction in central retinal thickness, reduction in total neovascular lesion size, reduction in subretinal hyperreflectivity material (SHM), gain in ETDRS letters, lack of new or persistent leaks, or lack of macular hemorrhage; and administering to the patient about 2 mg aflibercept at a dosing frequency of about every 9 to 12 weeks if the anatomic outcome is present in the patient compared to an initial evaluation; or administering to the patient about 2 mg of aflibercept at a dosing frequency of about every 4 to 7 weeks to the patient if the anatomic outcome is not present in the patient compared to an initial evaluation;

wherein, prior to evaluating whether the patient has the anatomic outcome, the patient has received an initial treatment comprising intravitreal injection with aflibercept and an initial evaluation of an anatomic outcome prior to the beginning of the initial treatment.

17. The method of claim 16, wherein the initial treatment comprises intravitreal injection with aflibercept for at least about 3 months.

18. The method of claim 16, wherein the initial treatment with aflibercept comprises administering to the patient about 2 mg of aflibercept by intravitreal injection about every 8 weeks.

19. The method of claim 16, wherein the initial treatment comprises intravitreal injection with aflibercept for at least about one year.

20. The method of claim 16, wherein the anatomic outcome is a reduction in central retinal thickness as measured by optical coherence tomography (OCT).

21. The method of claim 16, wherein the anatomic outcome is a resolution of subretinal fluid as measured by optical coherence tomography (OCT).

22. The method of claim 16, wherein the anatomic outcome is a reduction in total neovascular lesion size as measured by fluorescence angiography.

23. The method of claim 16, wherein the anatomic outcome is a reduction in subretinal hyperreflectivity material (SHM) as measured by optical coherence tomography (OCT).

24. The method of claim 16, wherein the anatomic outcome is a gain of ETDRS letters.

25. The method of claim 16, wherein the anatomic outcome is a gain of more than 5 ETDRS letters.

26. The method of claim 16, wherein the anatomic outcome is a gain of more than 15 ETDRS letters.

27. The method of claim 16, wherein the anatomic outcome is a lack of new or persistent leaks as measured by fluorescein angiography (FA).

28. The method of claim 16, wherein the anatomic outcome is a lack of macular hemorrhage.

* * * * *